(12) United States Patent
Orbay et al.

(10) Patent No.: US 7,780,710 B2
(45) Date of Patent: Aug. 24, 2010

(54) SYSTEM FOR STABILIZATION OF FRACTURES OF CONVEX ARTICULAR BONE SURFACES INCLUDING SUBCHONDRAL SUPPORT STRUCTURE

(75) Inventors: Jorge L. Orbay, Miami, FL (US); Javier E. Castaneda, Miami, FL (US); Cesare Cavallazzi, Miramar, FL (US)

(73) Assignee: Depuy Products, Inc., Warsaw, IN (US)

( * ) Notice: Subject to any disclaimer, the term of this patent is extended or adjusted under 35 U.S.C. 154(b) by 601 days.

(21) Appl. No.: 11/040,724

(22) Filed: Jan. 21, 2005

(65) Prior Publication Data
US 2005/0182405 A1    Aug. 18, 2005

Related U.S. Application Data

(60) Provisional application No. 60/538,589, filed on Jan. 23, 2004, provisional application No. 60/546,127, filed on Feb. 20, 2004, provisional application No. 60/598,110, filed on Aug. 2, 2004, provisional application No. 60/643,432, filed on Jan. 7, 2005.

(51) Int. Cl.
*A61B 17/80* (2006.01)

(52) U.S. Cl. ................ 606/286; 606/310

(58) Field of Classification Search ............ 606/53, 606/60, 62, 65, 69, 72–73, 86, 89, 63, 67, 606/68, 280, 286, 297, 310
See application file for complete search history.

(56) References Cited

U.S. PATENT DOCUMENTS

| | | |
|---|---|---|
| 1,091,674 A | 3/1914 | Lee |
| 2,077,804 A | 4/1937 | Morrison |
| 2,500,370 A | 6/1947 | McKibbin .............. 128/92 |
| 2,685,877 A | 8/1954 | Dobelle |
| 3,002,514 A * | 10/1961 | Deyerle .............. 606/67 |
| 3,489,143 A | 1/1970 | Halloran .............. 128/92 |
| 3,552,389 A | 1/1971 | Allgower et al. |
| 3,668,972 A | 6/1972 | Allgower et al. |

(Continued)

FOREIGN PATENT DOCUMENTS

CH     611147     5/1979

(Continued)

OTHER PUBLICATIONS

Orbay, Jorge L. MD, "Advances in Distal Radius Fixation", Orthopedic Technology Review—Surgical Innovations, vol. 5, No. 2, Mar./Apr. 2003.*

(Continued)

*Primary Examiner*—Eduardo C Robert
*Assistant Examiner*—Elana B Fisher
(74) *Attorney, Agent, or Firm*—Gordon & Jacobson, PC

(57) ABSTRACT

A fracture fixation system is provided for a fracture of a head portion of a long bone which has subchondral bone defining a convex articular surface. The system includes a plate element positionable on the long bone substantially opposite the head portion of the long bone and on a first side of the fracture, and a post element extending from the plate and into the head portion and across the fracture. A support structure for supporting of the subchondral bone of the articular surface is coupled to the post.

16 Claims, 28 Drawing Sheets

U.S. PATENT DOCUMENTS

| | | | |
|---|---|---|---|
| 3,716,050 A | 2/1973 | Johnston | |
| 3,779,240 A | 12/1973 | Kondo | |
| 3,791,380 A * | 2/1974 | Dawidowski | 606/68 |
| RE28,841 E | 6/1976 | Allgower et al. | |
| 4,219,015 A | 8/1980 | Steinemann | |
| 4,408,601 A | 10/1983 | Wenk | |
| RE31,628 E | 7/1984 | Allgower et al. | |
| 4,493,317 A | 1/1985 | Klaue | |
| 4,498,468 A | 2/1985 | Hansson | |
| 4,513,744 A | 4/1985 | Klaue | |
| 4,561,432 A | 12/1985 | Mazor | |
| 4,565,193 A | 1/1986 | Streli | |
| 4,622,959 A | 11/1986 | Marcus | |
| 4,632,101 A | 12/1986 | Freeland | |
| 4,721,103 A | 1/1988 | Freedland | |
| 4,733,654 A | 3/1988 | Marino | |
| 4,794,919 A | 1/1989 | Nilsson | 128/92 |
| 4,838,252 A | 6/1989 | Klaue | |
| 4,858,602 A | 8/1989 | Seidel et al. | 128/92 |
| 4,927,421 A | 5/1990 | Goble et al. | |
| 4,957,118 A | 9/1990 | Erlebacher | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,041,114 A | 8/1991 | Chapman et al. | |
| 5,085,660 A | 2/1992 | Lin | |
| 5,127,914 A | 7/1992 | Calderale et al. | |
| 5,129,901 A | 7/1992 | Decoste | |
| 5,151,103 A | 9/1992 | Tepic et al. | |
| 5,160,335 A | 11/1992 | Wagenknecht | |
| 5,180,383 A | 1/1993 | Haydon | 606/72 |
| 5,190,544 A | 3/1993 | Chapman et al. | 606/69 |
| 5,197,966 A | 3/1993 | Sommerkamp | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,324,291 A | 6/1994 | Ries et al. | |
| 5,364,398 A | 11/1994 | Chapman et al. | |
| 5,364,399 A | 11/1994 | Lowery et al. | |
| 5,458,654 A | 10/1995 | Tepic | 623/23 |
| 5,472,444 A | 12/1995 | Huebner et al. | 606/64 |
| 5,489,284 A | 2/1996 | James et al. | |
| 5,514,138 A | 5/1996 | McCarthy | |
| 5,531,748 A | 7/1996 | de la Caffiniere | |
| 5,578,035 A | 11/1996 | Lin | 606/68 |
| 5,601,553 A | 2/1997 | Trebing et al. | |
| 5,674,222 A | 10/1997 | Berger et al. | |
| 5,676,667 A | 10/1997 | Hausman | 606/69 |
| 5,702,399 A | 12/1997 | Kilpela et al. | |
| 5,709,686 A | 1/1998 | Talos et al. | 606/69 |
| 5,749,872 A | 5/1998 | Kyle et al. | 606/69 |
| 5,759,184 A | 6/1998 | Santangelo | |
| 5,776,194 A | 7/1998 | Mikol et al. | 623/16 |
| 5,796,139 A * | 8/1998 | Fukase | 257/315 |
| 5,797,913 A | 8/1998 | Dambreville et al. | |
| 5,810,820 A * | 9/1998 | Santori et al. | 606/63 |
| 5,810,823 A | 9/1998 | Klaue et al. | |
| 5,840,078 A | 11/1998 | Yerys | |
| 5,843,127 A | 12/1998 | Li | |
| 5,849,004 A | 12/1998 | Bramlet | |
| 5,882,351 A | 3/1999 | Fox | |
| 5,931,839 A | 8/1999 | Medoff | 606/69 |
| 5,938,664 A | 8/1999 | Winquist et al. | |
| 5,976,139 A * | 11/1999 | Bramlet | 606/66 |
| 5,993,449 A | 11/1999 | Schlapfer et al. | |
| 6,096,040 A | 8/2000 | Esser | 606/69 |
| 6,183,474 B1 | 2/2001 | Bramlet | |
| 6,183,475 B1 | 2/2001 | Lester et al. | |
| 6,206,881 B1 | 3/2001 | Frigg et al. | |
| D443,060 S | 5/2001 | Benirschke et al. | D24/155 |
| 6,270,499 B1 | 8/2001 | Leu et al. | 606/64 |
| 6,287,310 B1 | 9/2001 | Fox | |
| 6,322,562 B1 | 11/2001 | Wolter | |
| 6,358,250 B1 | 3/2002 | Orbay | 606/69 |
| 6,364,882 B1 | 4/2002 | Orbay | 606/69 |
| 6,379,359 B1 | 4/2002 | Dahners | 606/62 |
| 6,406,477 B1 | 6/2002 | Fujiwara | |
| 6,409,768 B1 | 6/2002 | Tepic et al. | 623/23.27 |
| 6,440,135 B2 | 8/2002 | Orbay et al. | 606/69 |
| 6,443,954 B1 | 9/2002 | Bramlet et al. | |
| 6,454,770 B1 | 9/2002 | Klaue | |
| 6,468,278 B1 | 10/2002 | Muckter | 606/69 |
| 6,527,776 B1 | 3/2003 | Michelson | |
| 6,558,388 B1 | 5/2003 | Bartsch et al. | |
| 6,562,042 B2 | 5/2003 | Nelson | |
| 6,579,294 B2 | 6/2003 | Robioneck | |
| D479,331 S | 9/2003 | Pike et al. | |
| 6,623,486 B1 | 9/2003 | Weaver et al. | 606/69 |
| 6,648,889 B2 | 11/2003 | Bramlet et al. | |
| 6,648,890 B2 | 11/2003 | Culbert et al. | |
| 6,669,701 B2 | 12/2003 | Steiner et al. | |
| 6,685,706 B2 | 2/2004 | Padget et al. | |
| 6,689,135 B2 | 2/2004 | Enayati | |
| 6,706,046 B2 | 3/2004 | Orbay et al. | |
| 6,866,665 B2 | 3/2005 | Orbay | 606/69 |
| 6,926,720 B2 | 8/2005 | Castaneda | |
| 2002/0032446 A1 * | 3/2002 | Orbay | 606/69 |
| 2002/0156474 A1 * | 10/2002 | Wack et al. | 606/69 |
| 2002/0161369 A1 | 10/2002 | Bramlet | |
| 2003/0004514 A1 | 1/2003 | Frigg et al. | |
| 2004/0002735 A1 * | 1/2004 | Lizardi et al. | 606/232 |
| 2004/0193162 A1 * | 9/2004 | Bramlet et al. | 606/66 |
| 2005/0010226 A1 | 1/2005 | Grady, Jr. et al. | 606/69 |

FOREIGN PATENT DOCUMENTS

| | | |
|---|---|---|
| DE | 8907443 | 9/1989 |
| DE | G 92 00 328.1 | 4/1992 |
| DE | 43 41 980 A | 6/1995 |
| DE | 43 43 117 A1 | 6/1995 |
| DE | 44 38 264 A1 | 3/1996 |
| DE | 93 21 544 U1 | 10/1999 |
| DE | 19857279 | 6/2000 |
| DE | 29907161 | 8/2000 |
| DE | 20200705 U1 | 3/2002 |
| EP | 0 207 884 A2 | 1/1987 |
| EP | 1 468 655 A2 | 10/2004 |
| FR | 2233973 | 1/1975 |
| FR | 2405062 | 5/1979 |
| FR | 2405705 | 5/1979 |
| FR | 2405706 | 5/1979 |
| FR | 2 606 268 | 5/1988 |
| JP | 04138152 | 5/1992 |
| SU | 1279626 | 12/1986 |
| WO | WO 97/09000 | 3/1997 |
| WO | WO 00/53110 | 9/2000 |
| WO | WO 00/53111 | 9/2000 |
| WO | WO 02/096309 A1 | 12/2002 |
| WO | WO2005/037117 | 4/2005 |

OTHER PUBLICATIONS

Zimmer Periarticular Plating System- Low-Profile Fixation (catalog). Zimmer, Inc., 2003. (8 pages).

The Mayo Clinic Congruent Elbow Plates (catalog). ACUMED. Hillsboro, OR: 2003. (20 pages).

Locking Compression Plate (LCP) System (brochure). SYNTHES. West Chester, PA: 2003. (6 pages).

Hessman et al., "Internal Fixation of Proximal Humeral Fractures: Current Concepts," European Journal of Trauma, 2003 No. 5, p. 253-261.

Osgood and Ahmad, "Two- and Three-Part Fractures of the Proximal Humerus," Shoulder and Elbow Trauma, 2004, Chapter 13, p. 169-182.

Philos, The Anatomical Fixation System for the Proximal Humerus with Angular Stability, XP-002205191, Jan. 1, 2001, pp. 1-3.

* cited by examiner

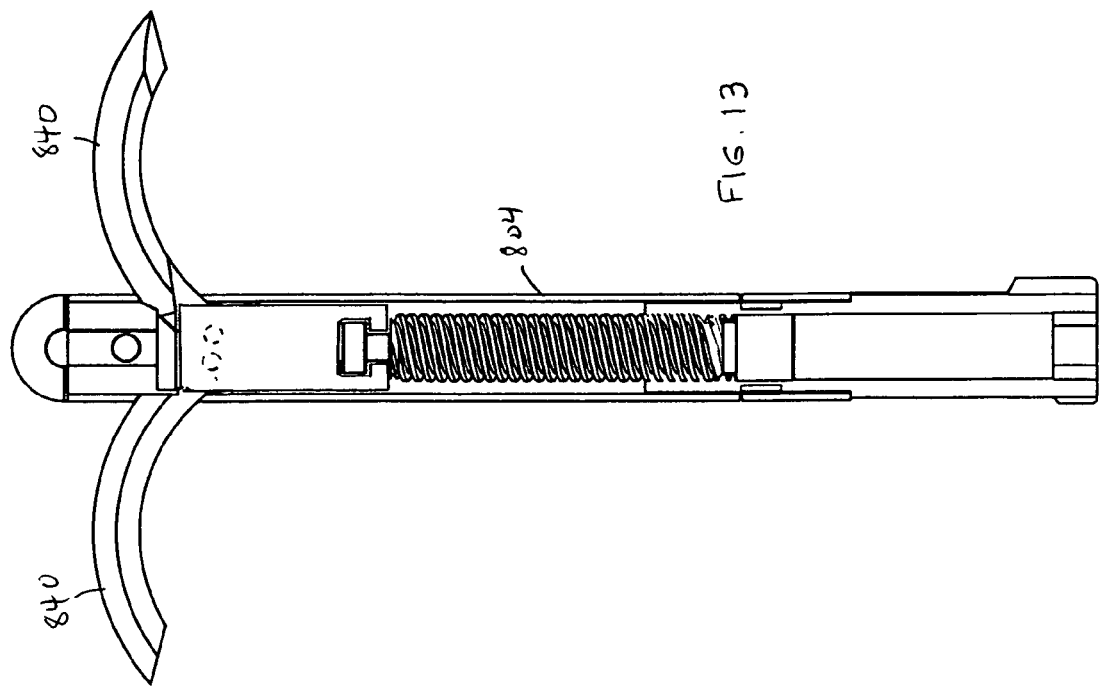
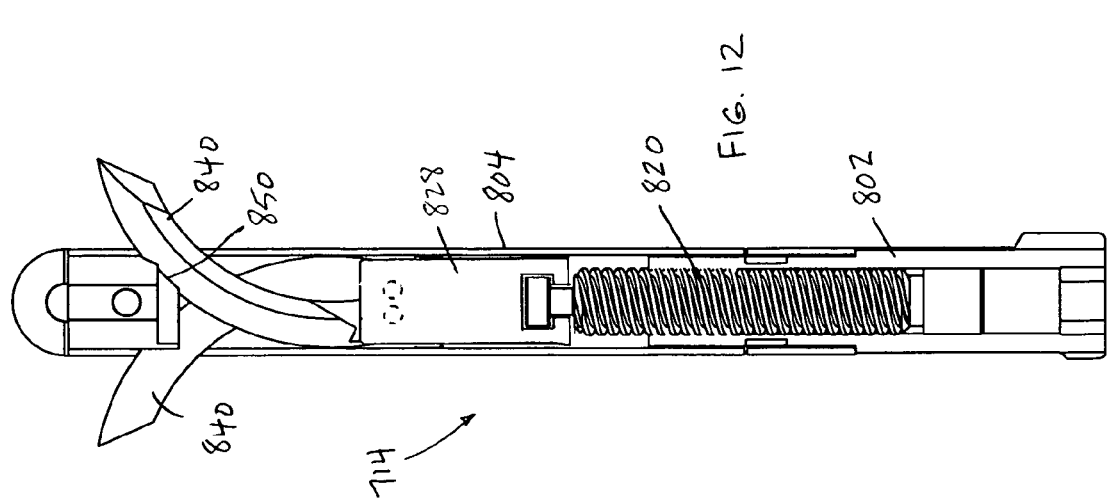

SYSTEM FOR STABILIZATION OF FRACTURES OF CONVEX ARTICULAR BONE SURFACES INCLUDING SUBCHONDRAL SUPPORT STRUCTURE

CROSS-REFERENCE TO RELATED APPLICATIONS

The application claims the benefit of U.S. Provisional Applications 60/538,589, filed Jan. 23, 2004, 60/546,127, filed Feb. 20, 2004, 60/598,110, filed Aug. 2, 2004, and 60/643,432, filed Jan. 7, 2005, which are hereby incorporated by reference herein in their entireties.

BACKGROUND OF THE INVENTION

1. Field of the Invention

This invention relates broadly to surgical devices. More particularly, this invention relates to a fracture fixation system including an orthopedic plate and associated fasteners for fastening the plate to the bone and tendons.

2. State of the Art

The proximal humerus comprises the upper portion of the humerus, i.e. upper arm of the human body, commonly known as the shoulder area. Fractures of the proximal humerus typically result from traumatic injuries such as sporting accidents and can be more frequent with age due to bone loss. Fractures of the proximal humerus are treated by exposing the fracture site and reducing the bone fracture and then placing a plate or other means onto the bone to fixate the fracture for healing in the reduced position. Reducing the fracture includes realigning and positioning the fractured portions of the bone to their original position or similar stable position. Fixating the fracture includes positioning a plate over the fractured portions and securing the plate onto the fractured bones and adjacent non-fractured bones with bone screws.

Conventional fixation plates have several shortcomings when applied to the proximal humerus. In general, they are not well shaped for the humeral anatomy, and when provided in a size necessary to provide the structural rigidity for stability of a humeral fracture are not easily shaped by the surgeon. Furthermore, such plates require large screws which do not provide purchase in underlying osteoporotic bone.

Two plates particularly contoured for the proximal humerus are the locking proximal humeral plate (LPHP) and PHILOS from Synthes of Paoli, Pa. These plates include a proximal head portion which receives several fixed angle fasteners which extend into the rounded head of the humerus perpendicular to the articular surface and threadably couple to the plate. Particularly in osteoporotic bone, there is a tendency for the fasteners to pierce the bone and enter the articular space between the head of the humerus and the shoulder socket which can cause significant irritation and potentially greater orthopedic damage. Such damage can interfere with, prolong, or prevent proper healing of the humeral fracture, in addition to causing the patient additional pain and the development of post-traumatic arthritis.

SUMMARY OF THE INVENTION

It is therefore an object of the invention to provide a humeral fracture fixation system which is anatomically appropriate for the humerus.

It is another object of the invention to provide a humeral fracture fixation system which provides a stable framework for support of a proximal humeral fracture.

It is a further object of the invention to provide a humeral fracture fixation system in which the fasteners extending through the plate will not break through the articular surface.

It is also object of the invention to provide a humeral fracture fixation system which facilitates alignment of fasteners into the head of the humerus.

It is yet another object of the invention to provide a humeral fracture fixation system which provides the surgeon a tactile sensation of when fasteners are properly implanted within the head of the humerus.

In accord with these objects, which will be discussed in detail below, a humeral fracture fixation system is provided and includes a plate, a plurality of cortical screws, and a plurality of posts for coupling the plate to the humerus and stabilizing the fracture. The system preferably also includes K-wires and suture material, as discussed below.

The plate is provided with a plurality of post holes. A post is provided for each post hole, and extends through the head portion of the plate generally perpendicular to the articular surface of the shoulder. According to a preferred aspect of the invention, a post may be provided with a support means for supporting the subchondral bone of the articular surface. When provided with such support means, the post includes a head which preferably can be fixed in a particular rotational orientation relative to the post hole so that the support means is always oriented in a particular orientation, and preferably in alignment with the anterior-posterior plane, relative to the plate and the anatomy.

According to another preferred aspect of the invention, the head portion includes a plurality of alignment holes which are sized to closely receive individual K-wires in a particular orientation. The orientation of axes through the alignment holes, and consequently K-wires inserted therethrough, closely conforms to the space defined by the posts when coupled to the head portion of the plate.

After the fracture is reduced and prior to drilling holes for the posts, the surgeon drills K-wires through the alignment holes on the head portion of the plate to temporarily fix the orientation of the head of the plate to the head of the humerus. Once the alignment is so fixed, the fracture is examined, e.g., under fluoroscopy, to determine whether the fracture is reduced in an anatomically correct manner and if the K-wires are properly aligned relative to the anatomy. The fluoroscopically viewed K-wires provide an indication as to whether the posts will be properly oriented in relation to the fracture and articular surface. If the placement is correct, the K-wires maintain the position of the plate over the fracture while holes are drilled for the posts. If placement is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation. Once the plate is properly positioned with the K-wires, the plate, posts, and support means, if provided, can be implanted, and the K-wires can be removed.

According to yet another preferred aspect of the invention, the head portion includes a lower proximal recess and a plurality of suture guides with holes thereabout. The recess raises the suture guides off the surface of the bone to allow the surgeon to pass a needle with suture material through the suture guides and between the plate and the bone to permit tendon and bone fragments to be sutured to the plate.

With the fixation system implanted, the posts are oriented perpendicular to the articular surface but do not extend far enough to break through the articular surface.

Additional objects and advantages of the invention will become apparent to those skilled in the art upon reference to the detailed description taken in conjunction with the provided figures.

BRIEF DESCRIPTION OF THE DRAWINGS

FIG. 12 is a longitudinal section view of the deployable post of FIG. 5, shown in a partially deployed configuration;

FIG. 13 is a longitudinal section view of the deployable post of FIG. 5, shown in a fully deployed configuration;

DETAILED DESCRIPTION OF THE PREFERRED EMBODIMENTS

Figure 1:
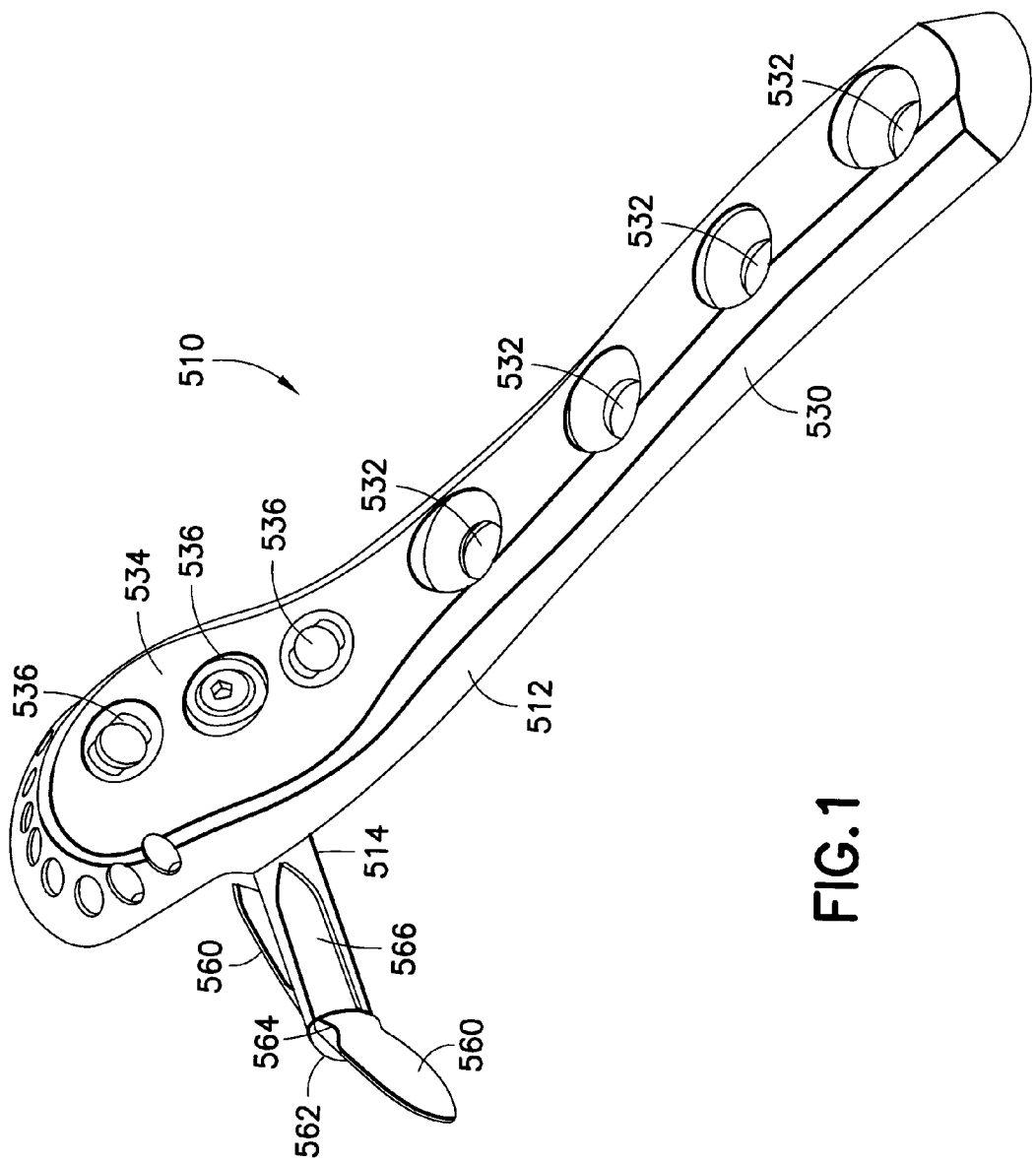
FIG. 1 is a perspective view of an embodiment of a proximal humeral fixation system according to the invention.
Figure 2:
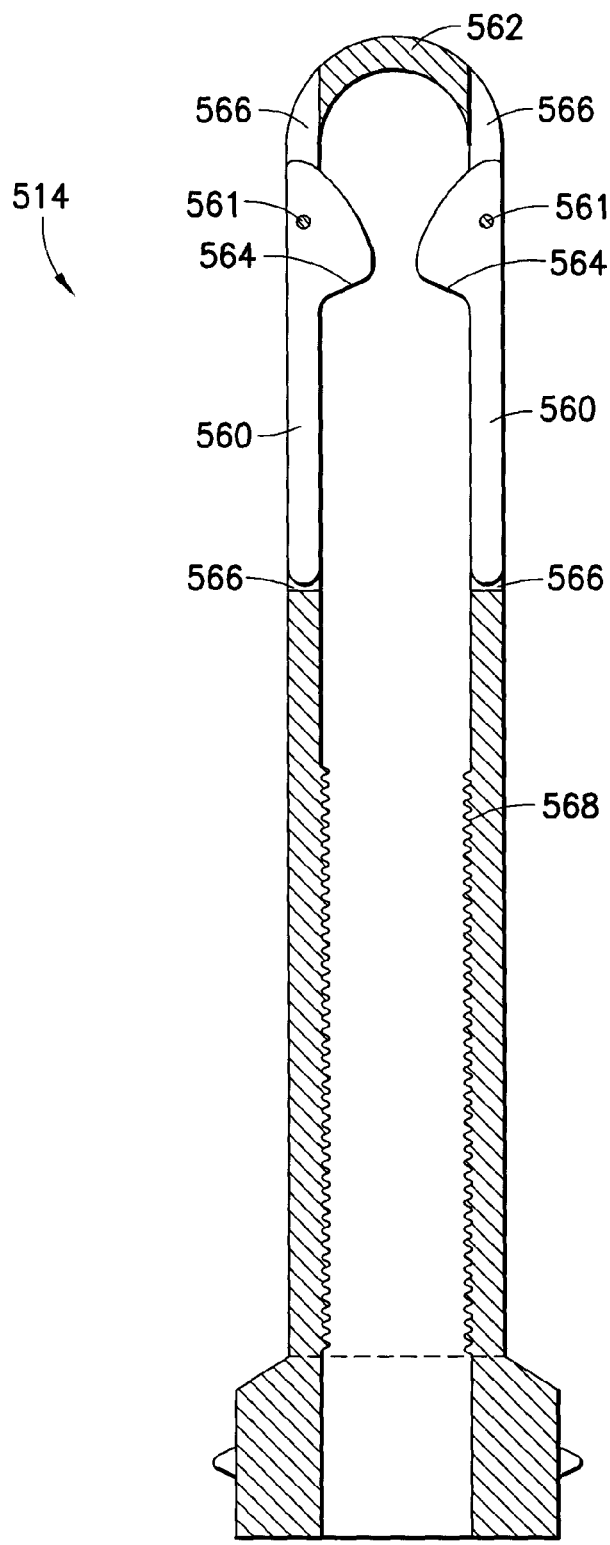
FIG. 2 is a schematic section view of a deployable post for the embodiment of FIG. 1, shown in a non-deployed configuration.

Turning now to FIG. 1, an embodiment of a proximal humeral fracture fixation system 510 according to the invention is shown. The system 510 includes a humeral plate 512 with one or more post holes 536 in a head portion 534 thereof and screw holes 532 along a shaft portion 530 thereof. A tubular post 514 is provided for each post hole 536. Referring to FIGS. 1 and 2, the post 514 includes a pair of arms 560 which are rotatably coupled about axes 561 adjacent the distal end 562 of the post 514. Embodiments with three or more arms may also be provided. Each arm 560 includes a cam follower surface 564 generally adjacent its pivot axis 561. When the cam follower surface 564 is subject to force in the distal and lateral directions, the arms 560 are moved into a radially open configuration, as shown in FIG. 1 and discussed further below. The post 514 includes windows 566 such that, when the arms 560 are in a closed position (FIG. 2), the arms 560 may lie flush with the remainder of the post. Referring to FIG. 2, the post also includes an internal thread 568.

Figure 3:
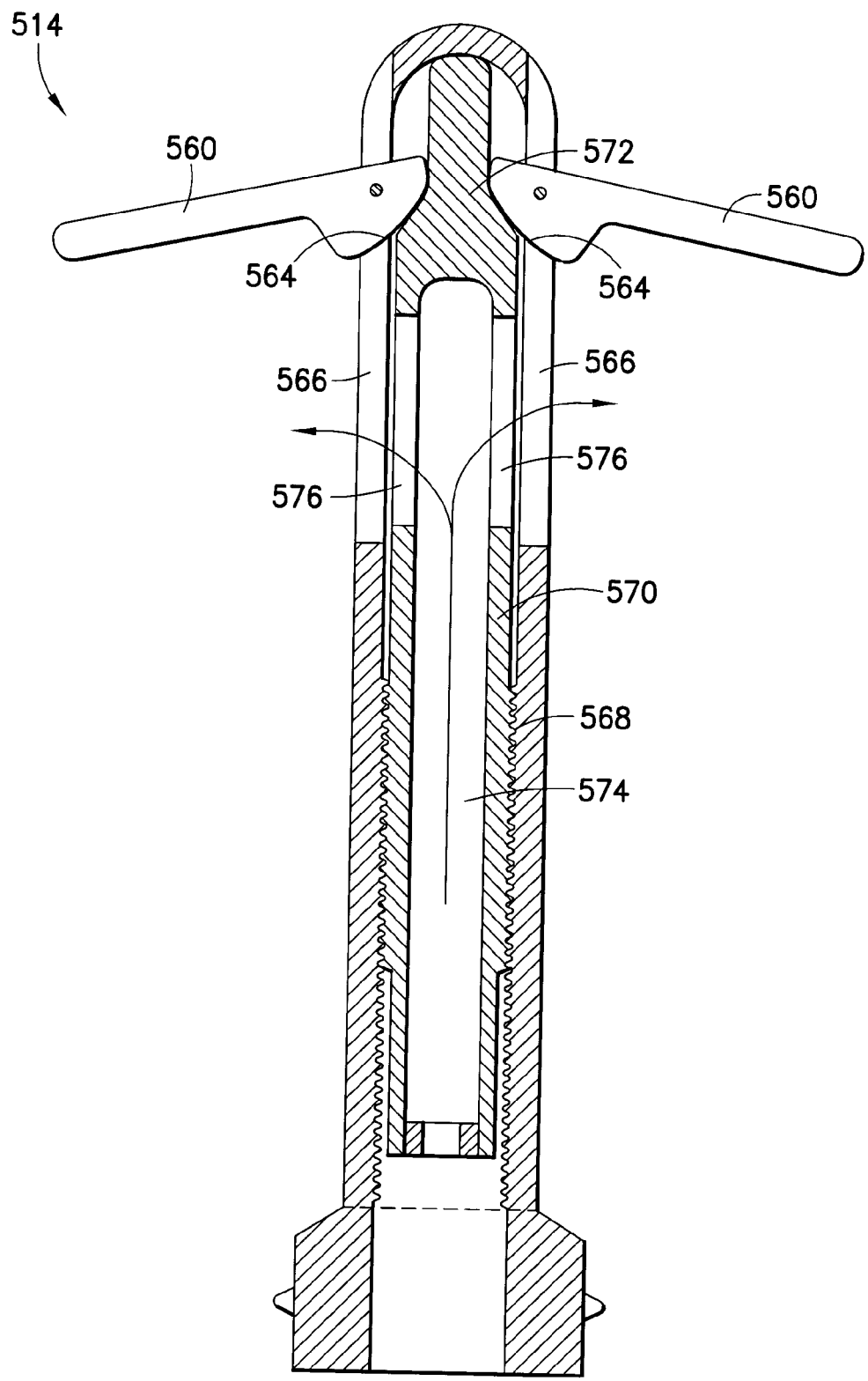
FIG. 3 is a schematic section view of a deployable post for the embodiment of FIG. 1, shown in a deployed configuration.

Referring to FIG. 3, a set screw 570 is provided which engages the internal thread 568 and includes a distal end provided with a cam 572 which operates to contact the cam follower surfaces 564 and move the arms 560 radially outward into the open configuration. In the open configuration, the arms 560 may each extend substantially 90° relative to the post 514; i.e., generally parallel to the articular surface and preferably in the anterior-posterior plane. However, it is even more preferable that the angle between each arm 560 and the post 514 be acute, and preferably approximately 60° to 89°, so that the arms better approximate the contour of the articular surface of the humeral head. While the arms 560 are surrounded by bone, the bone is often spongy or brittle osteoporotic bone which permits movement of the arms therethrough. The arms 560 shown are relatively broad providing significant stability to the fracture and support to the articular bone surface once moved into the open configuration. However, in order to facilitate movement through the bone, the arms may be relatively thinner than shown. Furthermore, the set screw may optionally include a bore 574 and distal openings 576 aligned with the windows 566 through which a preferably biodegradable bone cement or other preferably quick-setting filler material may be injected into the space created by the opening of the arms 560 (as shown by the arrows) to provide additional stability to the reduced fracture.

Figure 4:
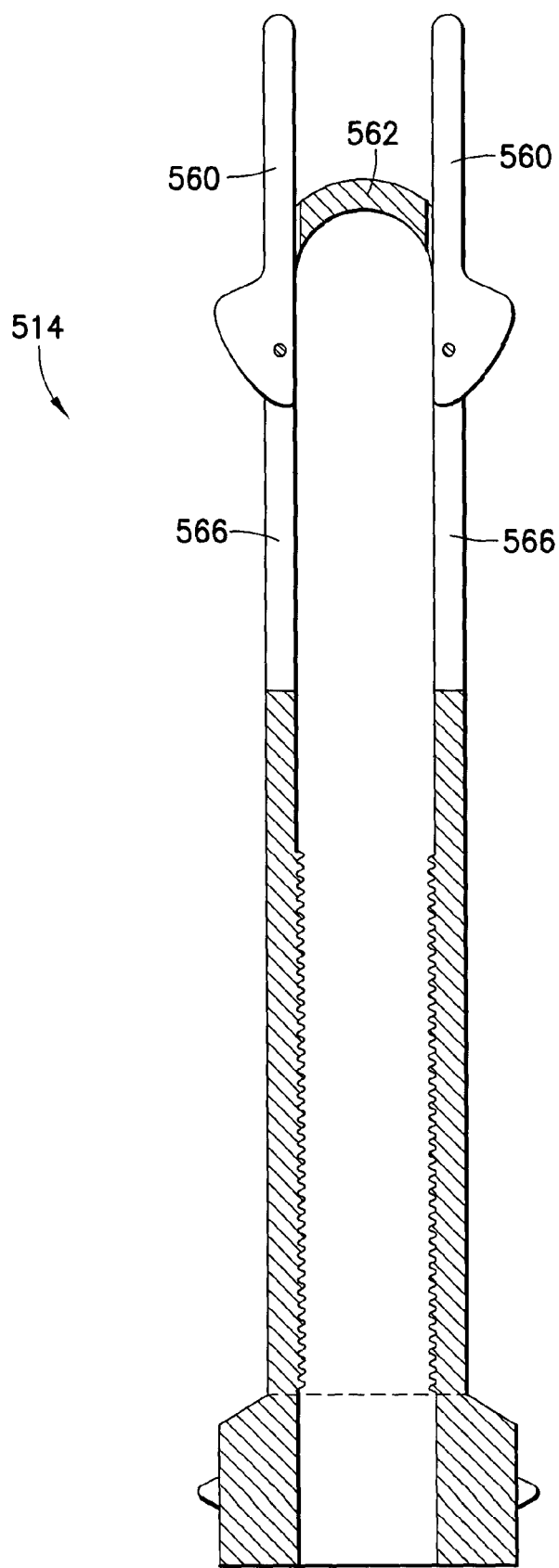
FIG. 4 is a schematic section view of a deployable post for the embodiment of FIG. 1, shown in a released configuration.

Referring to FIG. 4, if it is necessary or desirable to remove the post 514 and its arms 560 from the bone after implantation, the set screw 570 is unthreaded and removed from the post 514, and the post is then pulled from the bone. With the set screw 570 removed, the arms 560 are able to rotate upwards toward the upper end of the window 566 and stop against the distal end 562 of the post 514 as the post is withdrawn.

Figure 8:
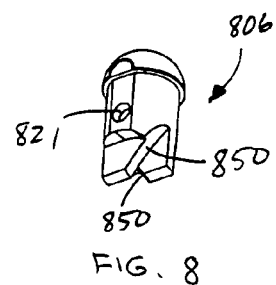
FIG. 8 is a perspective view of a distal tip of the deployable post of FIG. 5.

Turning now to FIGS. 5 through 11, another deployable post 714 is shown. The outer section of the post 714 includes a proximal tubular back end 802 (FIGS. 6A and 6B), a central tube 804 (FIG. 7) and a distal tip 806 (FIG. 8). Referring to FIGS. 6A and 6B, the back end 802 includes a head 807 with reference structure, e.g., scalloped notches 808, for rotationally orienting the post 802 relative to the humeral plate (as described in more detail below) and steps down to intermediate and smaller diameter portions 809, 810. The smaller diameter portion 810 defines two diametrically opposed wells 812. The distal end of the back end 802 further includes an internal thread 817. The tube 804 seats over the smaller diameter portion 810 and includes two distally directed wings 814 which engage in the wells 812 and lock the tube 804 on the back end 802 in a flush engagement with the intermediate diameter portion 809 of the back end 802. The tube 804 includes a pair of windows 852. The tip 806, also described further below, extends into the distal end of the tube 804 and is fixed in position on the tube with a pin 818 extending through holes 819, 821 in the tube 804 and tip 806, respectively.

Figure 5:
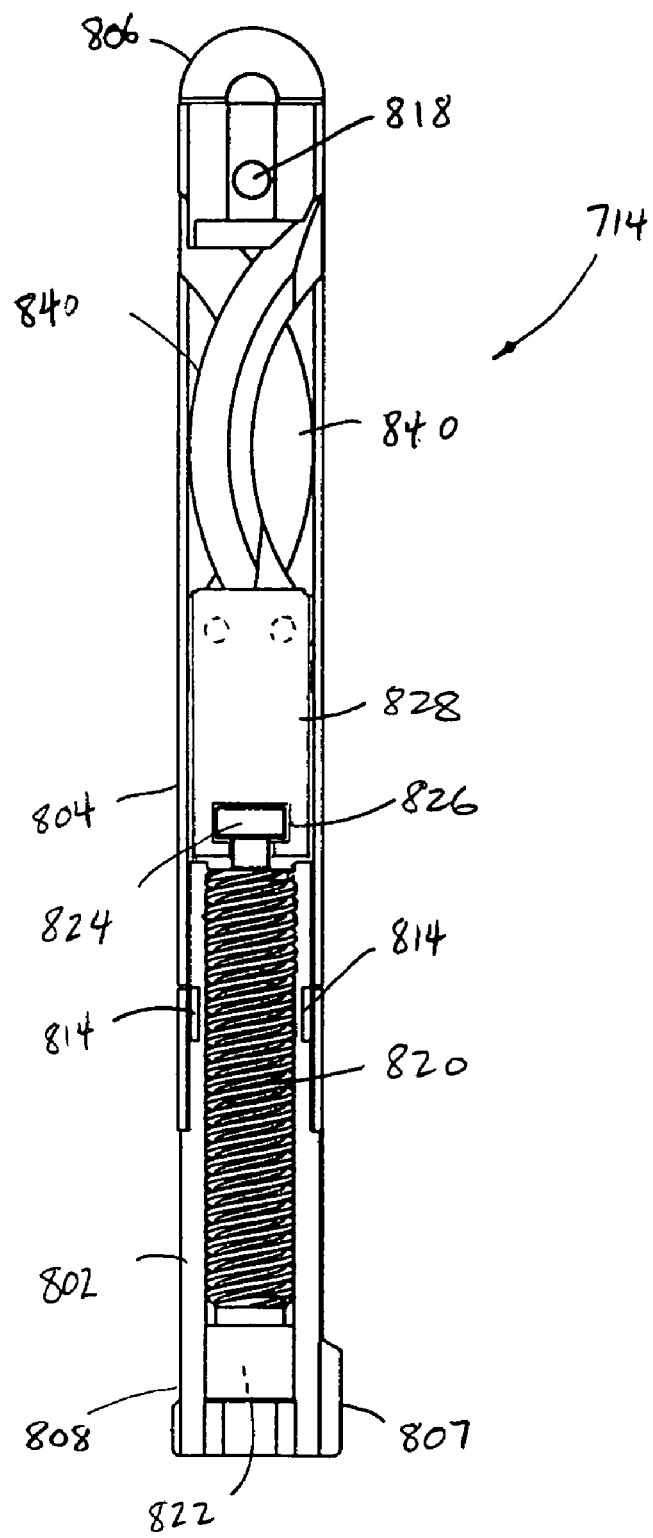
FIG. 5 is a longitudinal section view of another embodiment of a deployable post, with the deployable anchors in a non-deployed configuration.
Figure 6A:
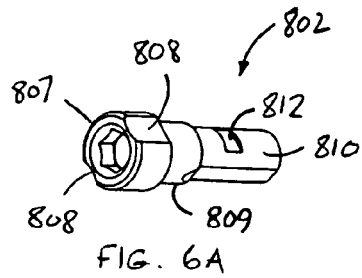
FIG. 6A is a perspective view of a back end of the deployable post of FIG. 5.
Figure 6B:
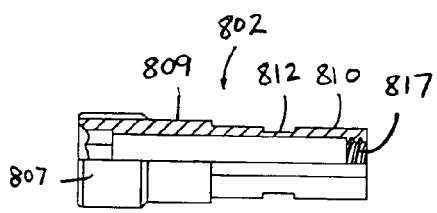
FIG. 6B is a longitudinal section view of the back end of the deployable post of FIG. 5.
Figure 7:
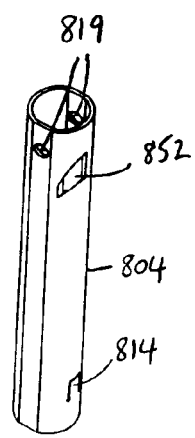
FIG. 7 is a perspective view of a central tube of the deployable post of FIG. 5.
Figure 9:
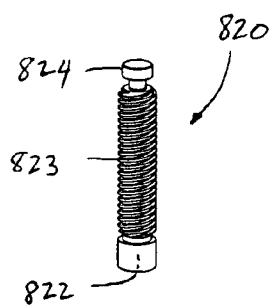
FIG. 9 is a perspective view of a lead screw of the deployable post of FIG. 5.
Figure 10:
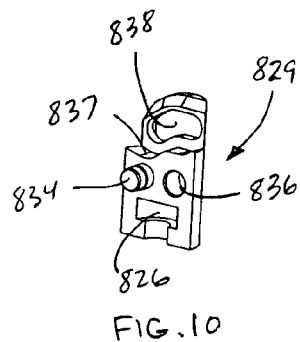
FIG. 10 is a perspective view of a coupler of the deployable post of FIG. 5.

Referring to FIGS. 5 and 9, a lead screw 820 is provided in the back end 802 of the post 714. The lead screw 820 includes a proximal engagement socket 822, e.g., square or hex socket, facilitating rotation of the lead screw 820 relative to the back end 802 by a tool, a threaded central portion 823 which engages the internal thread 817 of the back end 802, and a distal stepped head portion 824. The head portion 824 is captured by, and rotatable relative to, a nest 826 of a coupler 828. Coupler 828 is defined by a two hermaphroditic elements 829 (FIG. 10), which each include a post 834 and socket 836 which mate with corresponding parts on a like element. Each hermaphroditic element 829 also defines a track 837 and/or slot 838 into which a portion of an anchor 840 is movably coupled, as discussed below.

Figure 11:
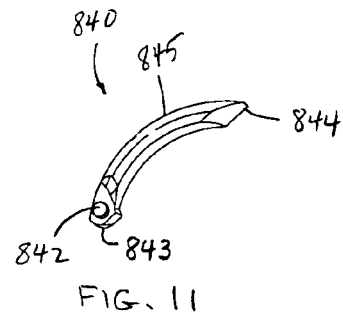
FIG. 11 is a perspective view of a bone anchor of the deployable post of FIG. 5.

Referring to FIG. 11, the bone anchors 840 include proximal axles 842 sized to travel within the slots 838 of the coupler 828 and have a back end 843 designed to ride along the track 837 of the coupler. The anchors 840 are curved along an arc, and each has a relatively sharp bone piercing end 844. The anchors are preferably made of metal, but may be made of ceramic or a stiff bioabsorbable material. Referring to FIGS. 8 and 11, the tip 806 defines two anchor guides 850 which each have a curvature corresponding to that of the convex side 845 of the anchors 840. The tube 804 defines two windows 852, corresponding to the cross-sectional shape of the anchors 840, through which the anchors 840 can be advanced out of the post 714.

Referring to FIGS. 12 and 13, the lead screw 820 is rotationally advanced through the back end 802 to thereby cause advancement of the coupler 828 through the tube 804. As the coupler 804 advances, the anchors 840 are pushed forward, contact the guides 850 and are deflected out of the windows 852 (FIG. 7) in an outward direction, i.e., generally transverse to the axis of the post 714. In accord with one aspect of the invention, as the anchors 840 move forward and rotate about axles 842, their axes of rotation within the tube 804 changes, particularly relative to the initial orientation shown in FIG. 5 (as indicated by the broken circular marks on the coupler). This is accommodated by the ability of the axles 842 to move laterally within the slots 838 of the coupler 828. Referring to FIG. 13, when fully deployed, the anchors 840 preferably project outwardly between 2 and 3.5 times the diameter of the tube 804. In a preferred embodiment, the tube 804 has a diameter of 4 mm, and the anchors 840 each project approximately 10 mm.

Figure 14:
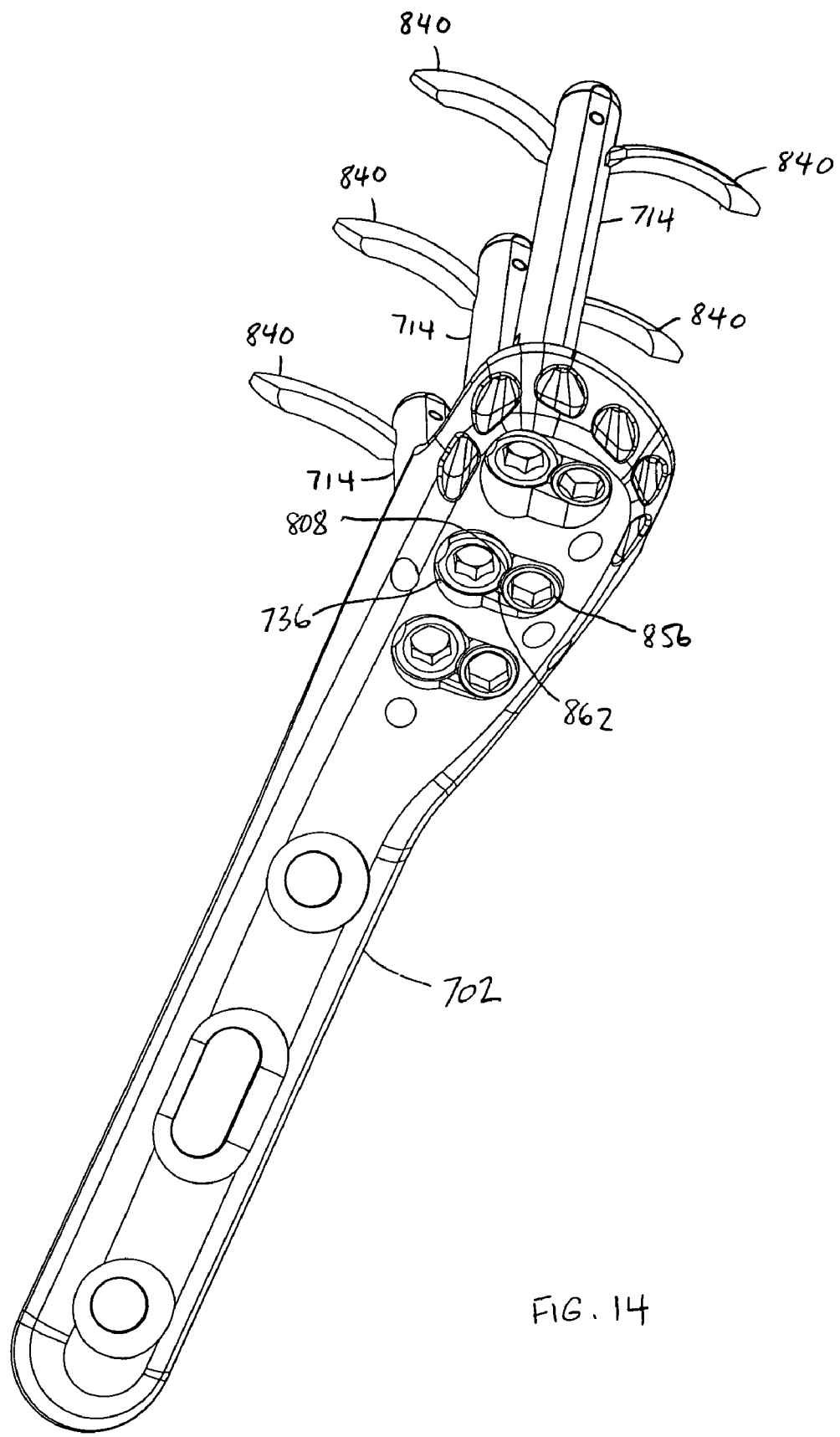
FIG. 14 is a perspective view of another system of the invention shown with deployable posts in the configuration of FIG. 13.

Turning now to FIG. 14, a humeral plate 702 is shown with a plurality of the posts 714 coupled thereto and with anchors 840 deployed. The posts 714 can be locked to the plate 702 in any suitable manner. However, it is preferable that the posts 714 be locked relative to the plate 702 so that the orientation of the deployed anchors 840 be predetermined, e.g., generally parallel to each other as shown. Moreover, it is preferable that each post 714 be locked relative to the plate 702 without a threaded coupling therebetween, as it is difficult to machine a threaded coupling in which (i) the components are both fixedly and rigidly coupled together, and (ii) in which the rotational orientation of the post can be predetermined with certainty upon locking Notwithstanding the above, it is certainly possible and within the scope of the invention to machine a threaded coupling between the post and the plate with the entry and termination points arranged and with the required tolerances to obtain the same results; i.e., predetermined rotational orientation upon fully seating the post in the plate.

In accord with a preferred aspect of the present embodiment, the lock between a post 714 and its respective post hole 736 preferably occurs within less than one complete rotation of the post 714 relative to the post hole 736, and more preferably within 0° to 90° rotation.

Figure 15:
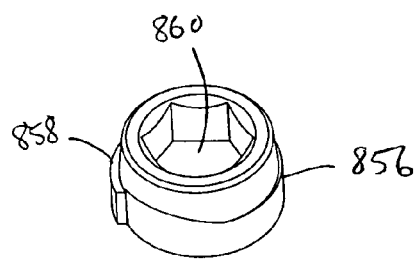
FIG. 15 is a perspective view of a cam for the system of FIG. 14.

One method of locking the posts is to use a cam to lock each post within the plate. Referring to FIG. 15, a preferred cam 856 is generally cylindrical, but has an outer wall 858 that spirally increases in radius about approximately 270° of the circumference of the cam. The cam 856 also includes a lower pin (not shown) about which the cam rotates, and an upper hex slot 860 for a driver.

Figure 17:
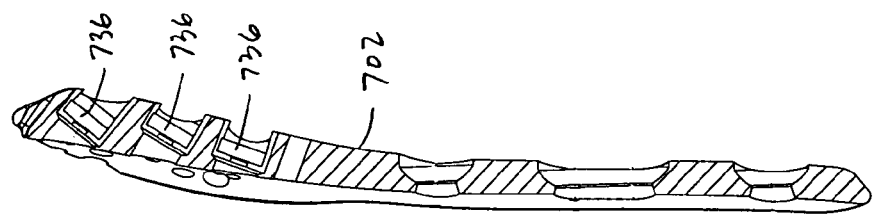
FIG. 17 is a longitudinal section view along line 17-17 in FIG. 16.
Figure 16:
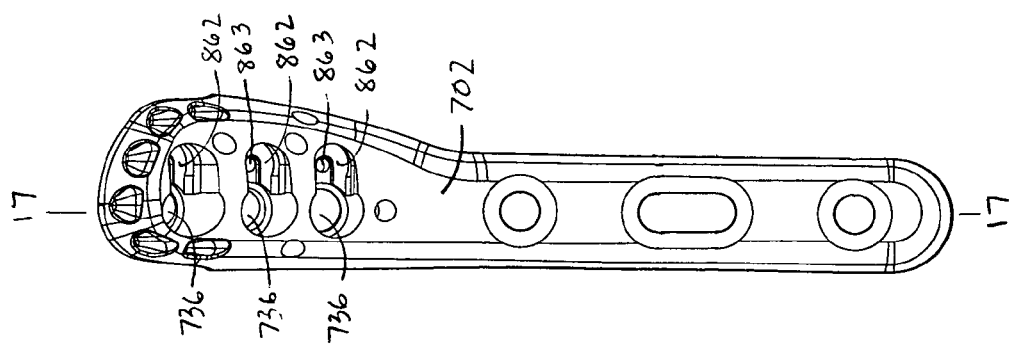
FIG. 16 is a plan view of the plate of the system of FIG. 14.

Referring to FIGS. 14, 16 and 17, for each post 714, the plate 702 includes a post hole 736 and an adjacent recessed cam slot 862 with a centering hole 863 which receives the centering pin. As a result of the shapes of the cam 856 and the cam slot 862, once the cam is received in the cam slot, the cam is essentially trapped therein. Before inserting the post 714 into the post hole 736, the cam 856 is rotated so that its smallest radius is positioned toward the post hole. The post 714 is received through the post hole 736, oriented so that a scalloped notch 808 at the back end 802 of the post fits about the outside of the cam 856, and pushed fully into the post hole. The cam 856 is then rotated with a driver to provide contact between a larger radiused portion of the cam and the post to provide sufficient contact therebetween to effectively lock the post 714 to the plate 702.

Figure 18:
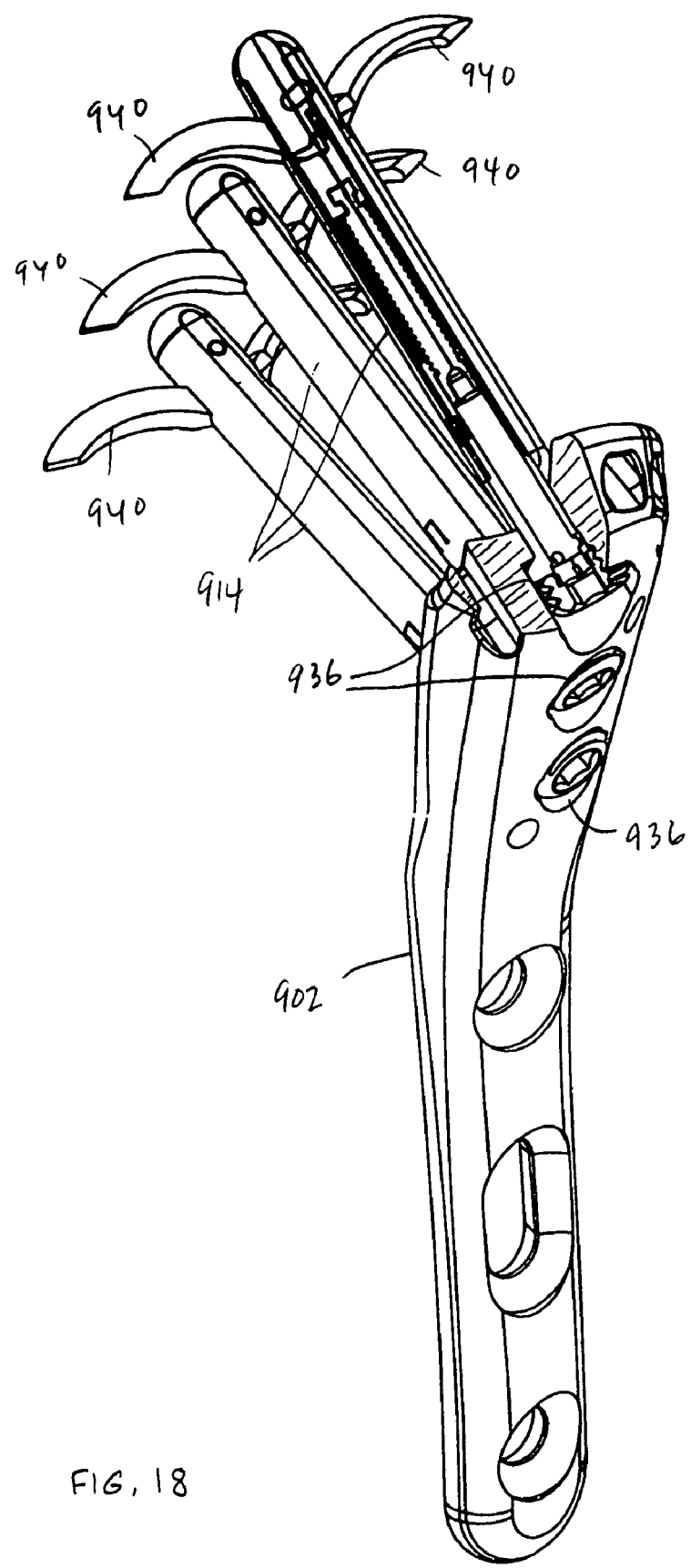
FIG. 18 is a perspective view of another system of the invention shown with the posts in a deployed configuration.
Figure 19:
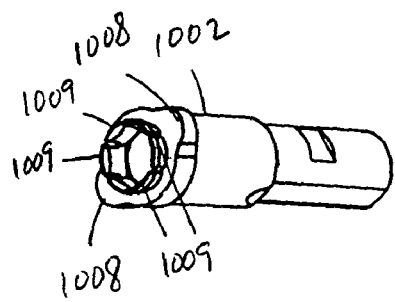
FIG. 19 is a perspective view of a back end of the deployable posts used in the system shown in FIG. 18.
Figure 20:
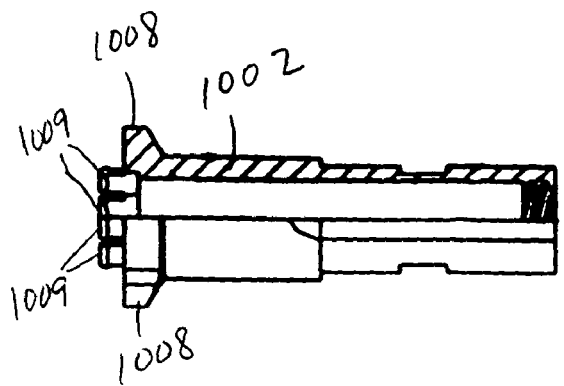
FIG. 20 is a longitudinal section view of the back end of the FIG. 19.
Figure 21:
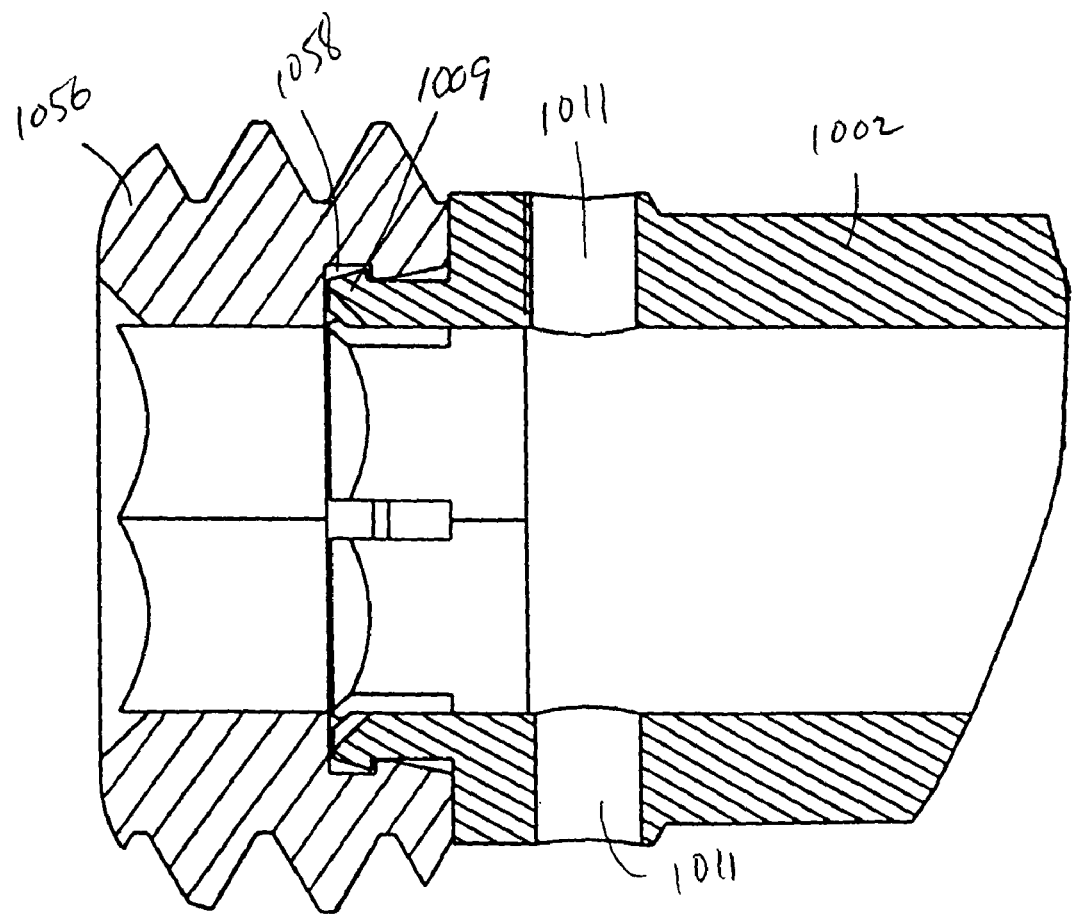
FIG. 21 is an enlarged broken section view of the back end and a set screw of the system shown in FIG. 18.

Turning now to FIGS. 18 through 20, another embodiment of a system for rotationally and axially locking the posts relative to the plate is shown. In accord with such system, the posts 914 are substantially as described above with respect to post 714. In contrast to post 714 (FIG. 5), the back end 1002 of the post 914 includes ears 1008 and a circular arrangement of resilient, radially outwardly directed catches 1009. In addition, referring to FIG. 21, the back end 1002 of post 914 includes a diametric bore 1011 to facilitate removal of an implanted post, if necessary, as described in more detail below. Still referring to FIG. 21, the system includes a set screw 1056 which locks the post 914 relative to the plate 902, as also described below. The set screw 1056 includes a recess 1058 in which the catches 1009 engage, but which also allows the set screw 1056 to be rotatable relative to the catches.

Figure 22:
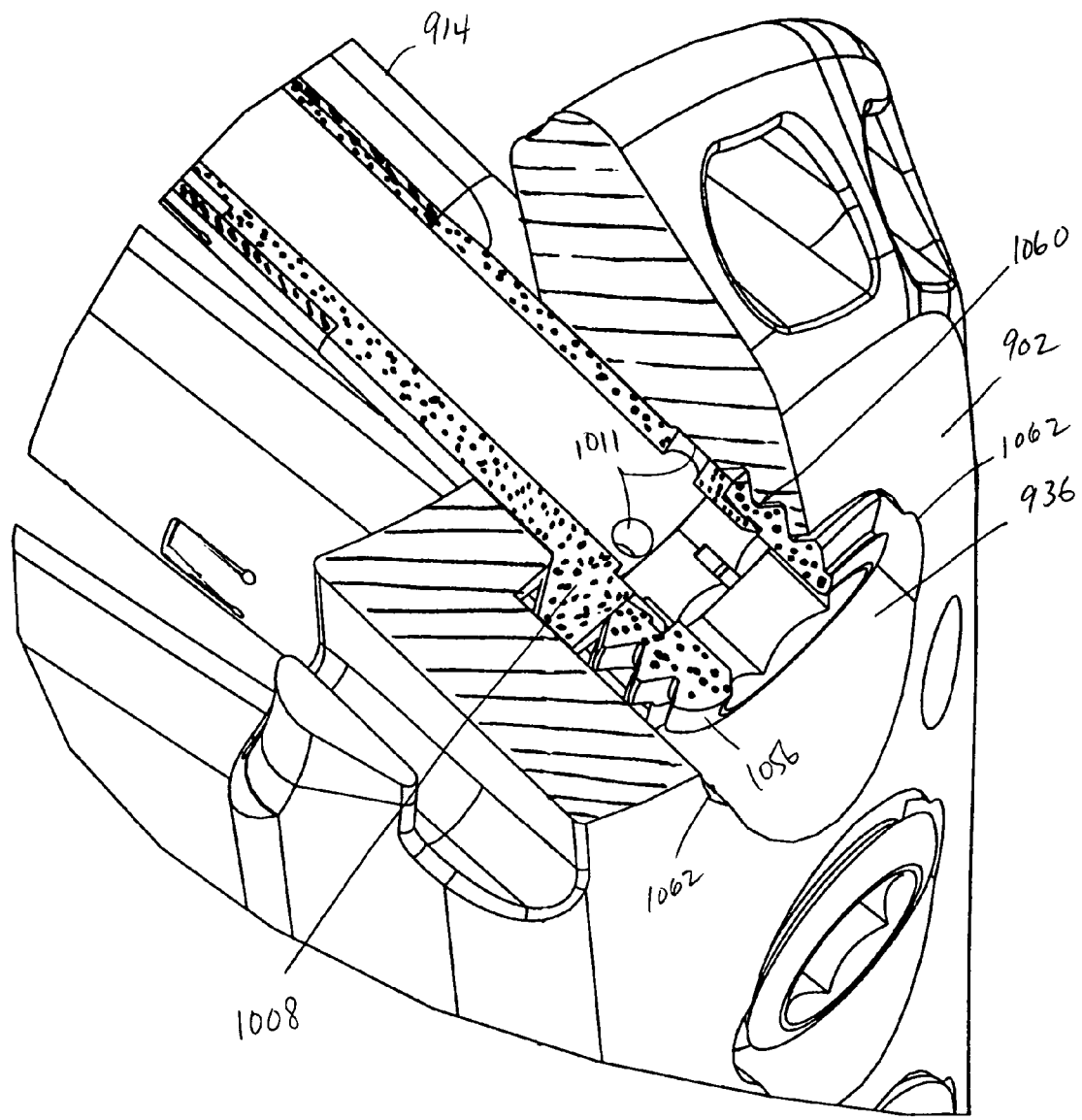
FIG. 22 is a broken partial section perspective view of the system shown in FIG. 18.

Referring now to FIG. 22, each post hole 936 of the plate 902 is stepped in diameter, includes threads 1060 within an upper larger diameter portion, and two diametric ear portions 1062. The post 914 is inserted through the post hole 936 so that the ears 1008 align with the ear portions 1062. This ensures proper alignment of the anchors 940 when they are later extended (FIG. 18). Then, the set screw 1056 is rotated in engagement with the threads 1060 and rotated until the post 914 is rigidly locked in place.

If necessary, to remove the post 914, the set screw 1056 is rotated into disengagement. In doing so, the set screw may release from the post. Should this occur, a tool (not shown) may be inserted into the diametric bore 1011 and pulled to withdraw the post from the bone and hole 936.

Figure 23:
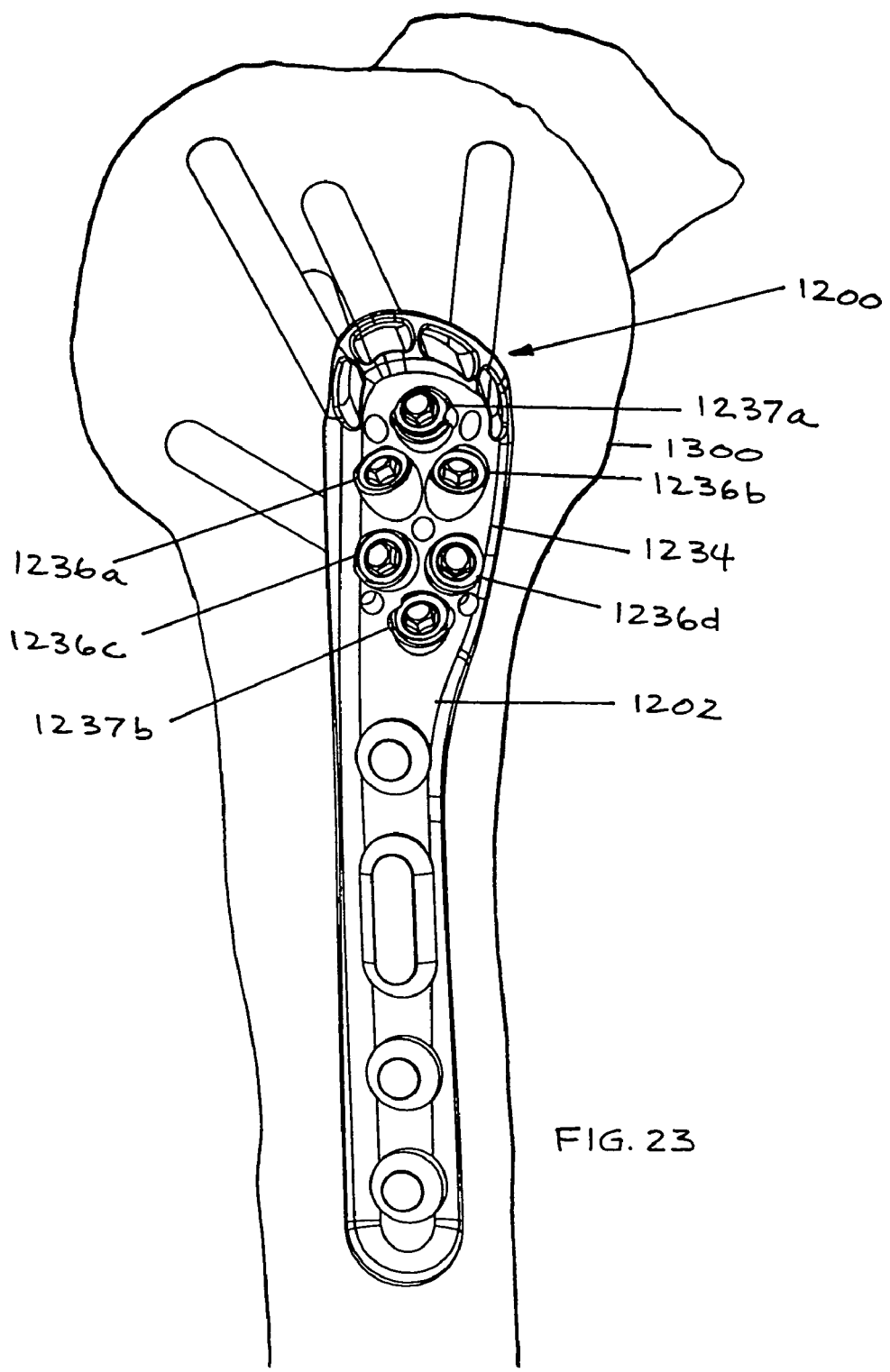
FIG. 23 is a lateral perspective view showing another embodiment of a proximal humeral fracture fixation system of the invention in place on the bone.
Figure 24:
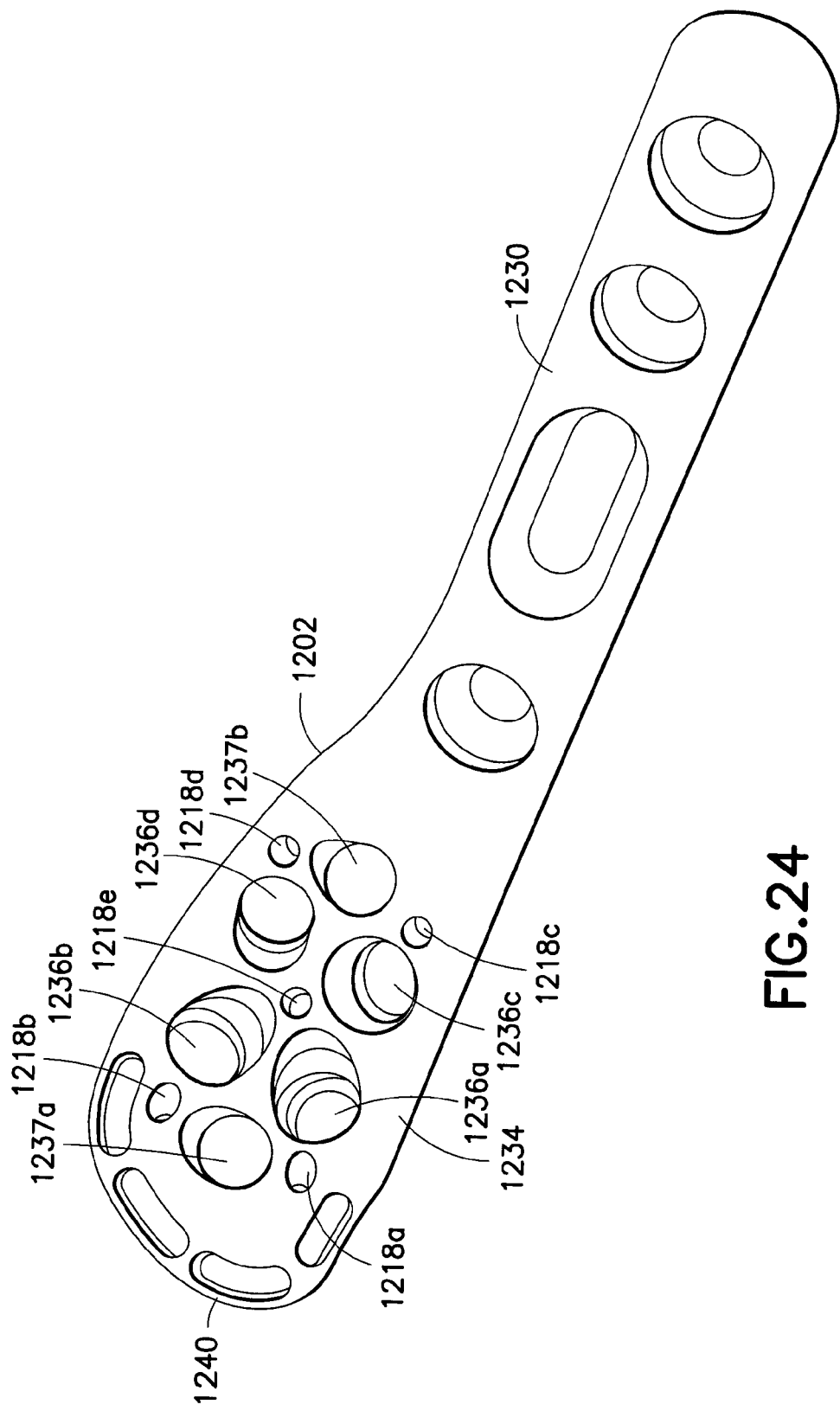
FIG. 24 is a perspective view of a plate of the system of FIG. 23.
Figure 25:
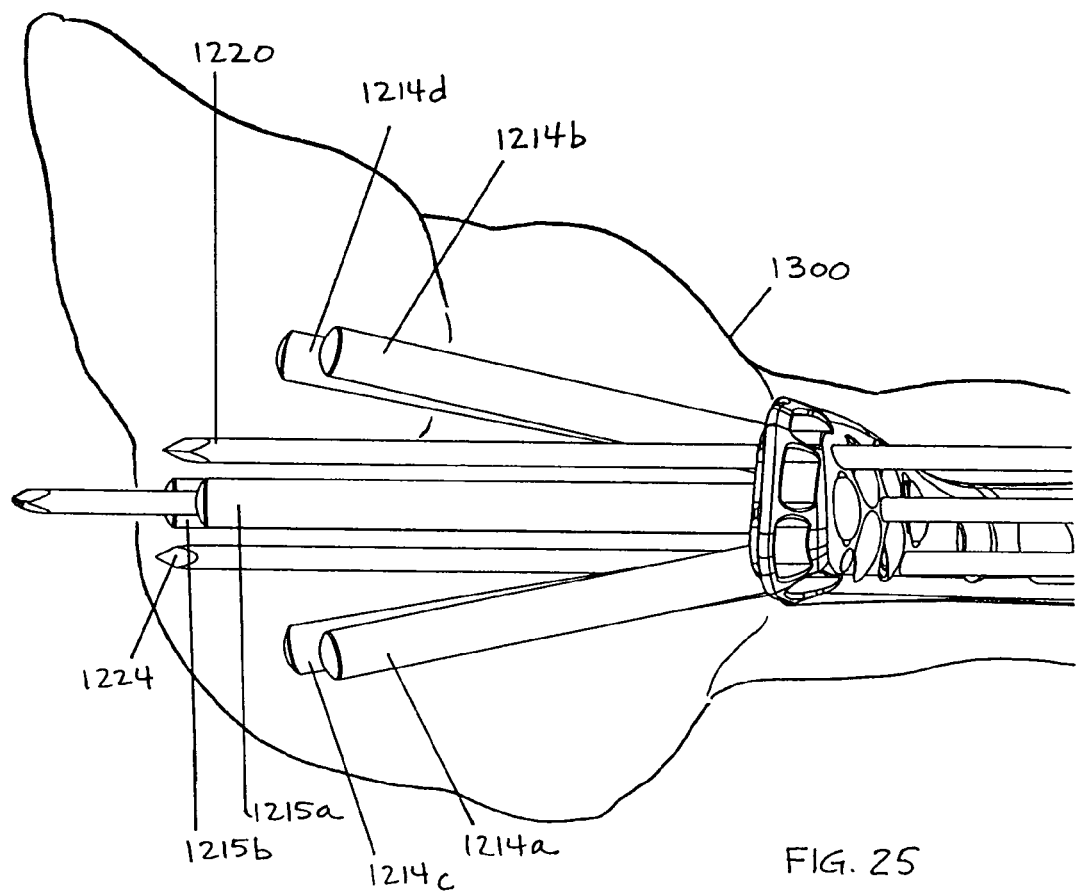
FIG. 25 is a top view of the fixation system of FIG. 23, shown implanted.
Figure 26:
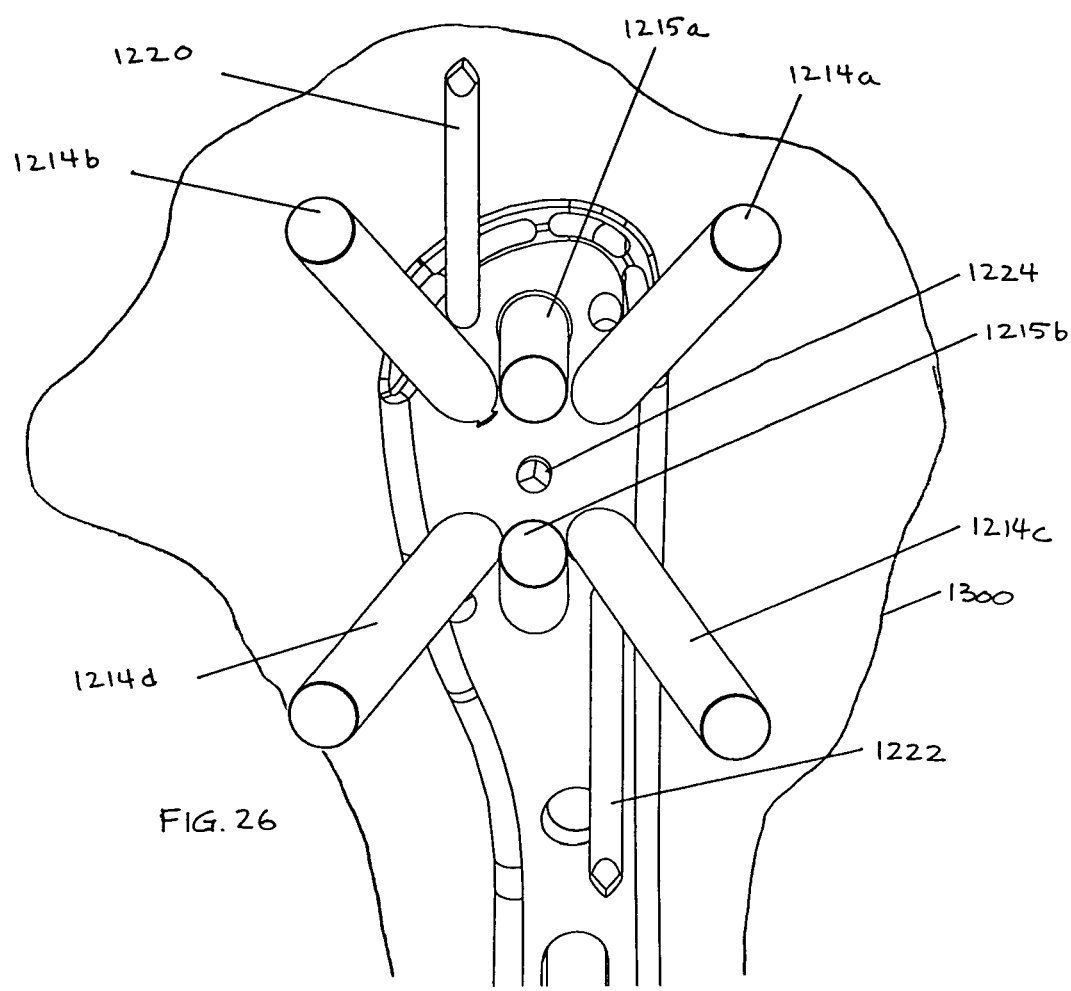
FIG. 26 is a medial view from within the bone of the fixation system of FIG. 23.

Turning now to FIGS. 23 through 28, another embodiment of a fixation system 1200 is shown attached to a humerus 1300. Referring to FIGS. 23 and 24, the system 1200 includes a plate 1202 having a head portion 1234 with six post holes, including central post holes 1236a, 1236b, 1236c, 1236d (collectively, 1236) designed to accept posts having a threaded head, and proximal and distal posts 1237a, 1237b (collectively, 1237) which are preferably substantially similar to post holes 936 (FIG. 22) for receiving posts which may optionally have deployable anchors. That is, post holes 1237 preferably include a system which locks the angular orientation of the post. Such system is also adapted to receive conventional threaded-head posts (with or without any deployable support means for supporting the subchondral bone of the articular surface), as shown in FIGS. 25 and 26. Further, where posts without any support means are used, the post holes do not require any system for angularly indexing or precisely fixing the posts. Referring still to FIGS. 25 and 26, the central post holes 1236a, 1236b, 1236c, 1236d define axes illustrated by the posts 1214a, 1214b, 1214c, 1214d therethrough which are angularly oblique from each other, causing the posts to diverge both laterally and longitudinally. The proximal and distal post holes 1237a, 1237b define axes which are preferably laterally aligned and angularly convergent, as illustrated by posts 1215a, 1215b.

Referring to FIG. 24, the head portion 1234 is also provided with five alignment holes 1218a, 1218b, 1218c, 1218d, 1218e (collectively, 1218), each sized to closely receive a K-wire (substantially smaller than a respective post for the post holes) along a fixed axis. Specifically, the axis of 1218e is directed toward the center of the articular surface of the humeral head. The alignment holes 1218 are angularly oriented within the head portion 1234 of the plate so as to present a path for K-wires which will outline various boundaries of the posts or identify a point of interest relative to the implanted posts. More particularly, as shown in FIGS. 24 through 26, K-wires 1220, 1222 positioned in holes 1218b, 1218c define the upper and lower bounds of posts 1214a, 1214b, 1214c, 1214d, while K-wire 1224 positioned in hole 1218e is directed to the center of the articular surface and defines a central location towards which the axes of the proximal and distal post holes 1215a, 1215b converge.

Figure 27:
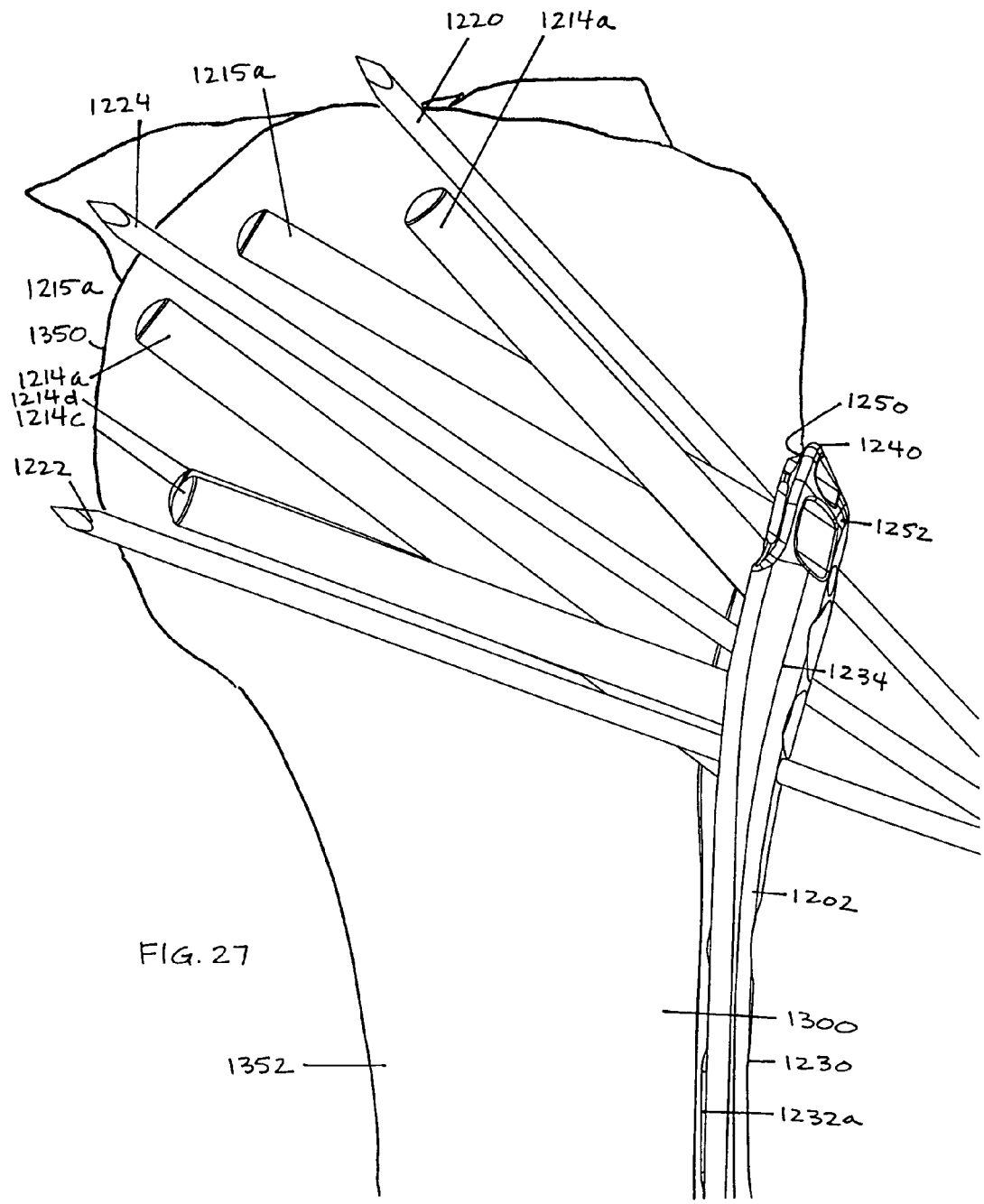
FIG. 27 is another view of the implanted fixation system of FIG. 23.

As shown best in FIGS. 24 and 27, a narrow suture rail 1240 extends about the proximal portion of the head portion 1234. The suture rail 1240 is elevated relative to the lower surface 1250 of the head portion to facilitate entry of a suture needle through the rail and recessed relative to the upper surface 1252 to present a relatively low unobtrusive profile.

Figure 28:
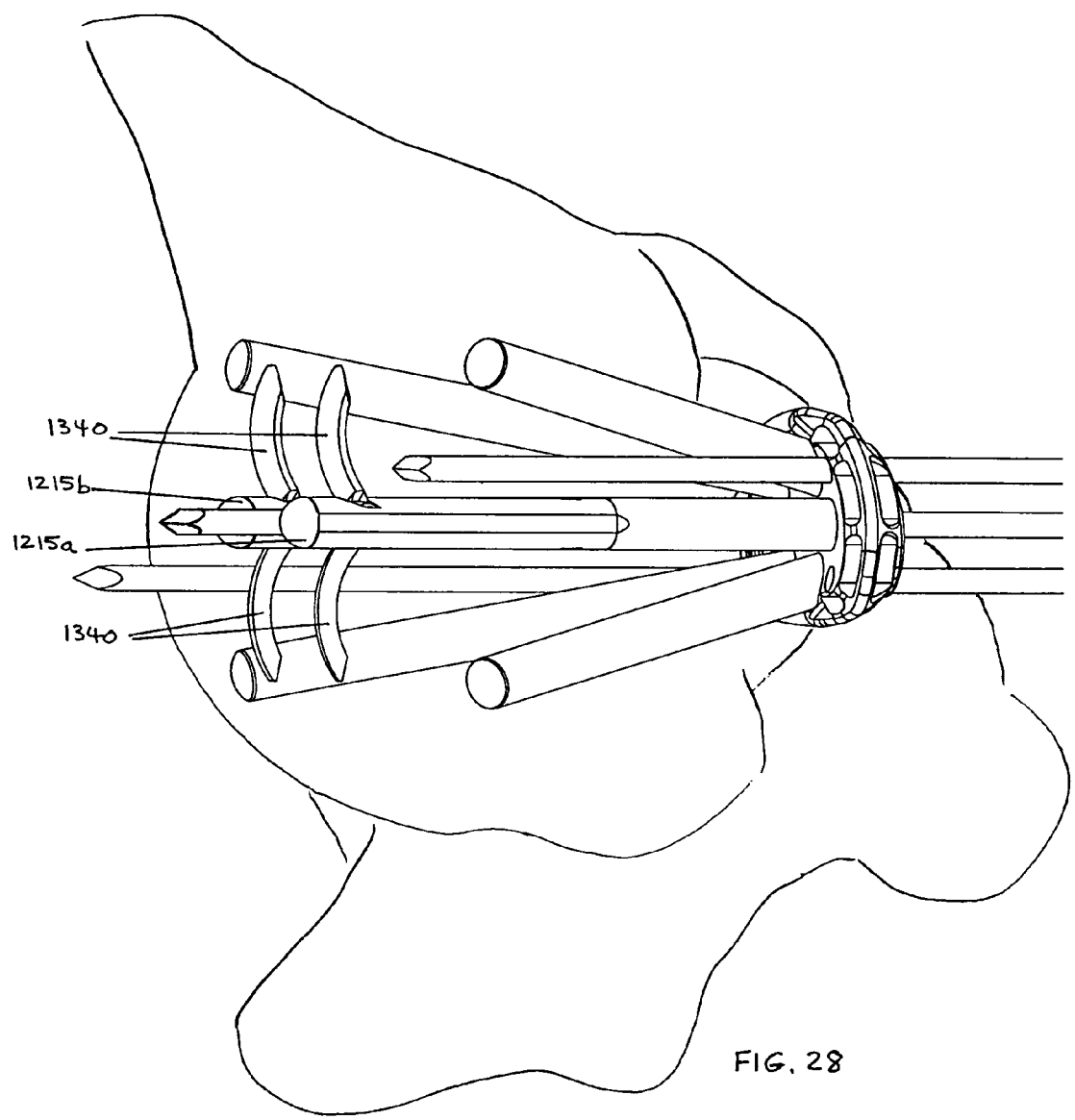
FIG. 28 is a view similar to FIG. 25 showing the system with deployed anchors.
Figure 29:
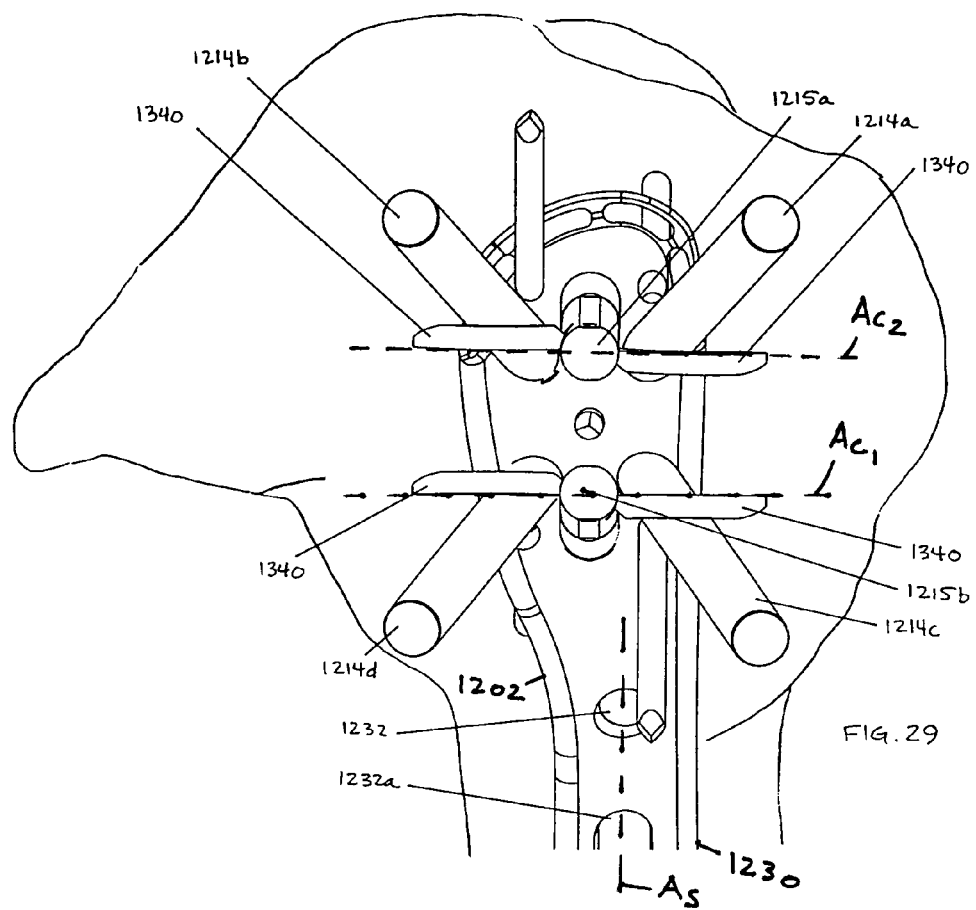
FIG. 29 is a view similar to FIG. 26 showing the system with deployed anchors.

Referring to FIGS. 27 through 29, in use, by way of a delto-pectoral approach, the fracture is exposed and debrided. Traction and direct manipulation are used to reduce the fracture, and the anatomical relationship between the articular surface of the subchondral bone 1350 and the humeral shaft 1352 is restored in both its angular alignment and retroversion. The position for the plate 1202 is then located on the humerus 1300, preferably immediately posterior to the intertubercle groove and approximately 1.5-2.0 cm below the insertion of the supraspinatus. The plate is then provisionally secured to the distal fragment using, e.g. 2.0 mm fixation K-wires inserted through the shaft of the plate or a cortical screw provisionally inserted through a non-locking oblong screw hole 1232a. The reduction is then locked by using K-wires 1220, 1222, 1224 inserted through the fixed angle K-wire holes on the head portion 1234 of the plate and into the proximal fragment(s). Multiple wires may be used to anticipate final post positions.

Axes of the alignment holes correspond to axes of adjacent post holes. Using preferably both anterior-posterior and axillary views, the K-wires 1220, 1222, 1224 are viewed fluoroscopically to provide an indication as to whether the posts will be properly oriented. If the placement is correct, the K-wires maintain the position of the plate over the fracture. The posts holes may then be drilled with confidence that their locations and orientations are proper. If placement is not optimal, the K-wires are removed and the surgeon can relocate the plate and/or can reorient the K-wires and drills again. Since each K-wire is of relatively small diameter, the bone is not significantly damaged by the drilling process and the surgeon is not committed to the initial drill location and/or orientation. The use of alignment holes and K-wires therethrough for an orthopedic plate is described in more detail in U.S. Ser. No. 10/689, 797, filed Oct. 21, 2003, U.S. Ser. No. 10/664,371, filed Sep. 17, 2003, and U.S. Ser. No. 10/985,598, filed Nov. 10, 2004, which are hereby incorporated by reference herein in their entireties.

The shaft 1230 of the plate 1212 is then fixed to the humeral diaphysis 1352 by fully inserting the cortical screw through the oblong hole 1232a. Any K-wires that may have been used to secure the shaft are removed.

Using a drill guide (not shown), holes for the posts are drilled. Using a depth gauge (not shown), the depth of the drilled holes is determined. Appropriate length posts 1214a, 1214b, 1214c, 1214d, 1215a, 1215b are inserted using a driver. The distal end of the posts are preferably 4-6 mm below the articular surface of the subchondral bone 1350. Radiographic confirmation of the correct fracture reduction and post placement is then made.

Referring to FIGS. 28 and 29, where the posts 1215a, 1215b include deployable anchors, the surgeon deploys the anchors 1340 to provide support for the articular surface of the subchondral bone 1350. As shown in FIG. 29, axes $A_{C1}$, and $A_{C2}$ through the deployed anchors are substantially parallel to each other and transverse to a longitudinal axis $A_S$ through the shaft portion 1230 of the plate 1202. In practice, the K-wires 1220, 1222, 1224 in the head portion 1234 are preferably removed prior to anchor deployment.

Additional holes are also drilled for the remaining cortical screws that will be used to fix the distal part of the plate to the diaphysis 1352 of the humerus.

Next, if necessary, tuberosities are reduced and fixed to the suture rail 1240 of the plate using sutures or wires.

Final radiographic views are then taken and the surgical wound is closed using appropriate surgical technique.

Figure 30:
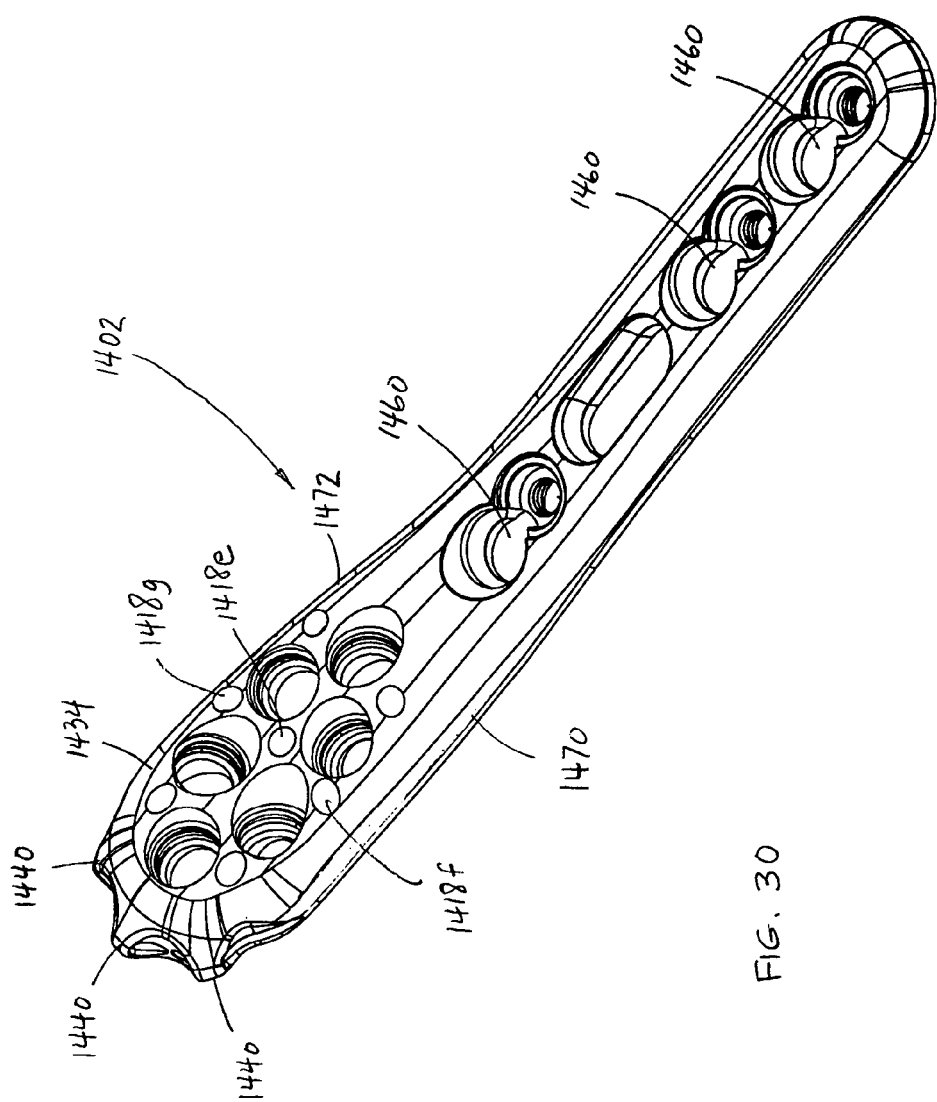
FIG. 30 is a perspective view showing another embodiment of a proximal humeral fracture fixation system of the invention.

Turning now to FIG. 30, another embodiment of a shoulder plate 1402 is shown. The plate 1402 is substantially similar to plate 1202 in features, but includes several significant structural distinctions. First, the proximal end of the head portion 1434 includes three discrete generally radially-arranged suture guides 1440 with lateral openings. The guides 1440 are spaced to permit needle access therethrough without obstruction from the adjacent guide(s). Second, additional K-wire openings 1418f, 1418g are provided anterior and posterior the central K-wire opening 1418e to permit the use of additional K-wires for fluoroscopic visualization of the arrangement of the posts within the bone prior to insertion of the posts. The additional openings 1418f, 1418g may be particularly useful where the surgical approach creates difficulty in the use of one of more of the other openings. Third, the bone screw holes 1460 are designed for use with specific cortical screws and set screws (not shown) which permits independent application of compression and locking of the cortical screw. Such screw holes, cortical screws and set screws, as well as other suitable screw systems which may be used in the fracture fixation systems described herein, are described in U.S. Ser. No. 11/040,779, filed simultaneously herewith, which is hereby incorporated by reference herein in its entirety.

It is noted that none of the shoulder plates are universal models, as the above described plate is adapted for placement on the left arm or the right arm, but not both. In accord therewith, each of the plates includes a substantially straight edge. When the head portion of the plate is positioned 1.5-2.0 cm below the insertion of the supraspinatus and the straight edge is aligned immediately posterior with the intertubercle groove, proper placement of the plate on the humerus is assured. For example, in FIG. 30, the straight edge is edge 1470, and opposite is a slightly curved edge 1472. The other shoulder plates described herein include corresponding straight and curved edges and when placed according to the above teaching provide the desired placement. Moreover, by locating the head portion of the plate at such a large distance relative to the insertion of the supraspinatus (which is in distinction from the significantly closer spacing in the prior art) the potential for interference between the head portion of the plate and the acromion when the arm is raised is minimized.

Figure 31:
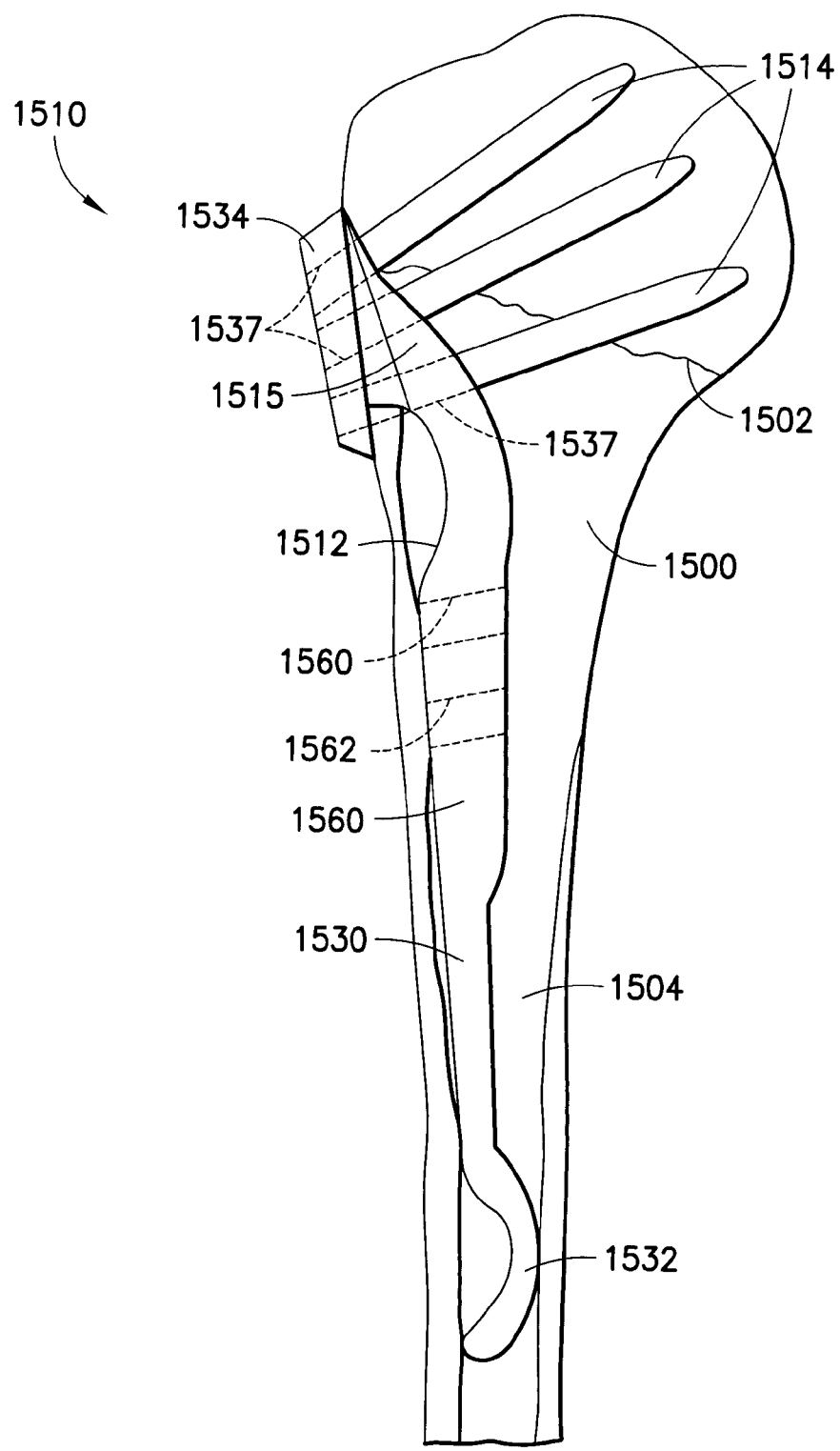
FIG. 31 is a schematic section view of a nail-plate embodiment of a proximal humeral fixation system according to the invention.

Referring to FIG. 31, another embodiment of a humeral fracture fixation system 1510 is shown coupled to a shoulder 1500, with the posts 1514 extending across a fracture 1502. The system 1510 includes a device 1512 having a plate-like head portion 1534, a neck 1515, and a shaft 1530. The neck 1515 of the device is attached to the head portion 1534 so as to seat intrafocally just below the fracture 1502. As a result of the forward location of the neck 1515, one or more of the post holes 1537 in the plate-like head portion 1534 extends through the neck 1515. The post holes 1537 are preferably axially angularly offset relative to each other. In contrast to the prior embodiments, the shaft portion 1530 of the device 1512 defines an intramedullary nail sized to be inserted intrafocally (through the fracture) and then be received within the medullary canal of the proximal humerus. Thus, the device 1512 is a "nail-plate." The shaft portion 1530 preferably extends from a lower central location of the head portion 1534, in distinction from the inferior end thereof. The shaft portion 1530 preferably tapers to facilitate entry into the medullary canal and terminates in a smooth bend 1532 which facilitates intrafocal entry of the end of the shaft, and further insertion into the medullary canal 1504. In addition, the shaft portion 1530 is preferably offset relative to the head portion 1534, as the shaft portion 1530 is intended to reside within the bone and the head portion 1534 is intended to reside on the surface of the bone. Holes 1560, 1562 are provided in the shaft portion for receiving fasteners. The holes 1560, 1562 are preferably threaded, and thus adapted to receive machine screws which can pull the shaft portion 1530 against the cortex of the bone. Alternatively non-threaded holes may be used, and standard cortical screws provided to couple the shaft to the humeral cortex. "Nail-plates" are described in more detail in co-owned U.S. Ser. No. 10/315,787, filed Dec. 10, 2002, which is hereby incorporated by reference herein in its entirety.

Turning now to FIGS. 32 through 35, another embodiment of a proximal humeral fixation system 2010 for fixation of a humeral fracture 2011 (FIG. 35) of the left arm is shown. The system 2010 includes a humeral plate 2012, and a plurality of rigid posts 2014, rigid cross pegs 2016, set screws 2018, and cortical screws 2019, all for coupling the plate 2012 to the humerus 2020 (FIG. 35) and stabilizing the fracture. The system 2010 may also include K-wires 2022 and suture material 2024, as discussed below.

Figure 32:
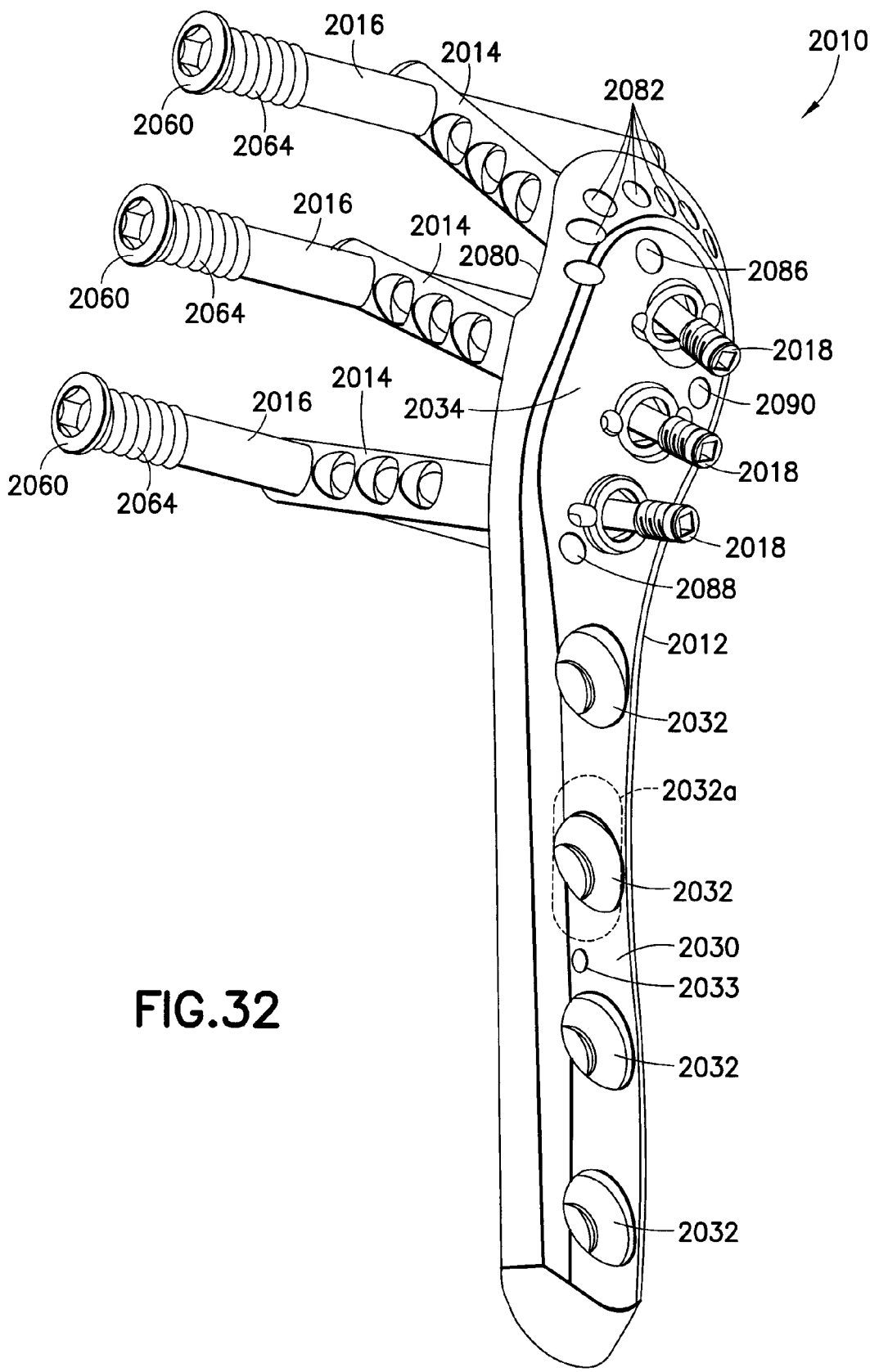
FIG. 32 is a perspective of an embodiment of a proximal humeral fracture fixation system according to the invention, shown with a humeral plate, posts, transverse cross pegs, and set screws.
Figure 33:
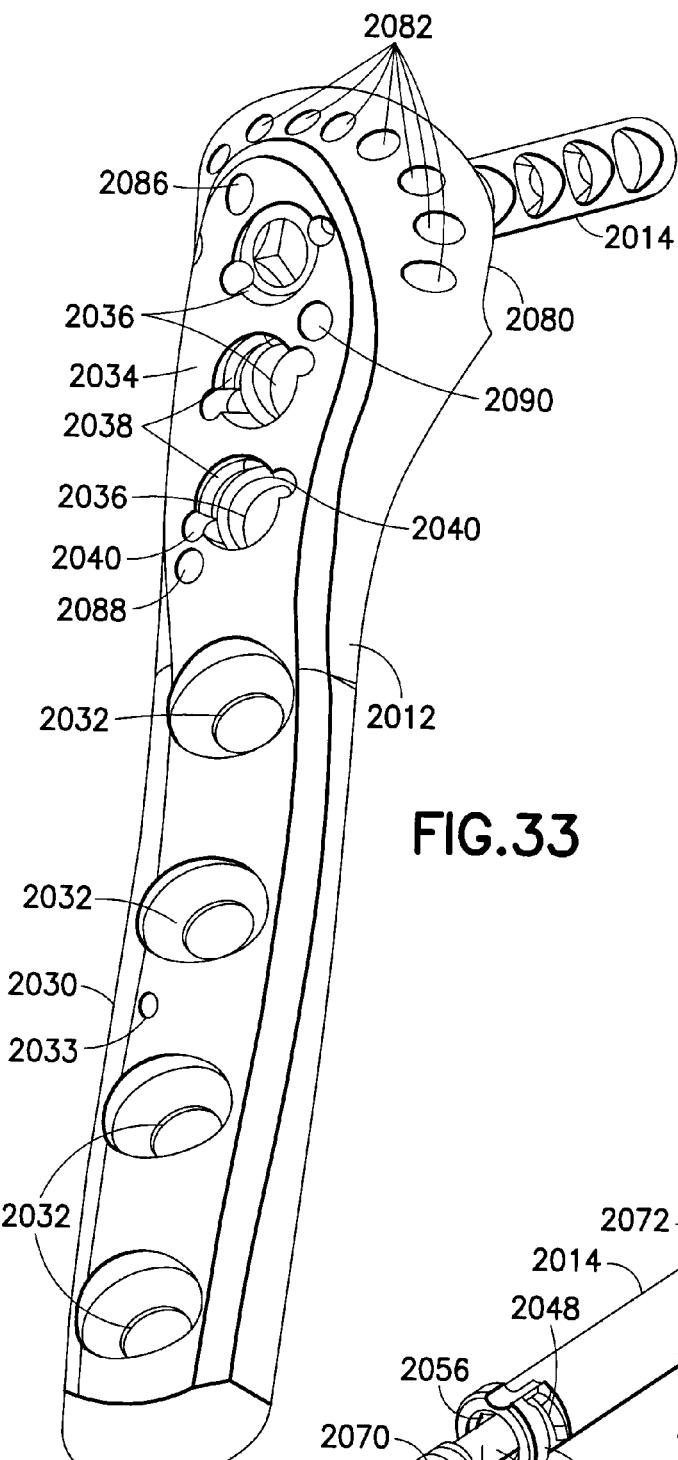
FIG. 33 is another perspective view of the first embodiment of FIG. 32, showing the humeral plate provided with one fixation post.
Figure 34:
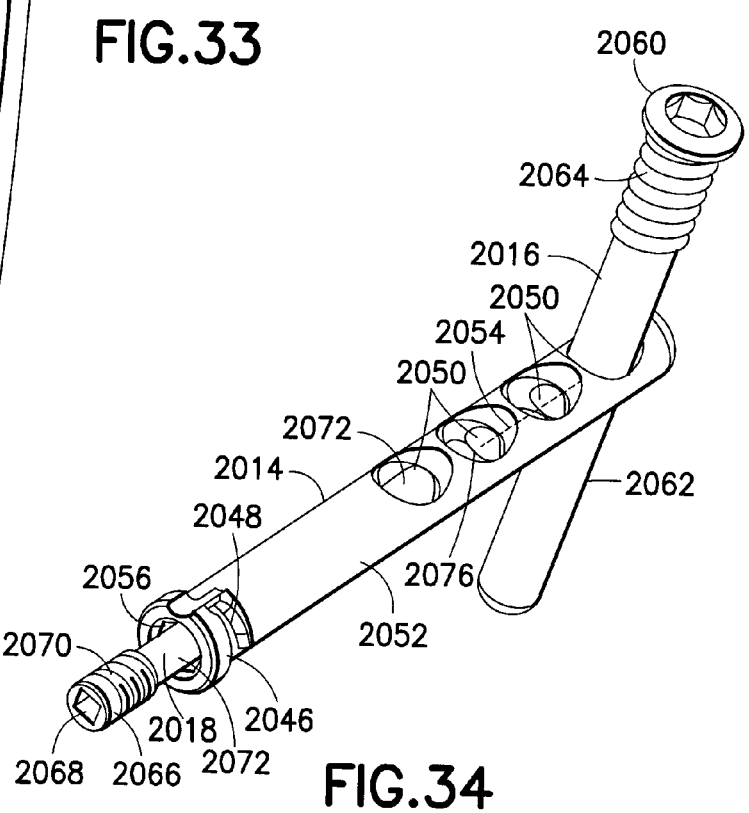
FIG. 34 is a perspective view showing the relationship between a fixation post, a transverse cross peg, and a set screw.

Referring to FIGS. 32 through 34, the humeral plate 2012 has a shaft portion 2030 and a head portion 2034. The head portion 2034 is angled slightly relatively to the shaft portion to properly seat on the humeral anatomy. The shaft portion 2030 includes screw holes 2032, one of which may be slotted or oblong (as indicated by dotted line 2032a in FIG. 32) to permit the plate 2012 to be longitudinally moved relative to a screw placed therethrough. The shaft portion may also include one or more K-wire holes 2033. The head portion 2034 is provided with post holes 2036. As indicated by the posts 2014 in FIG. 32, axes through the post holes 2036 are preferably substantially in a common plane but preferably diverge from each other within the common plane. According to a preferred embodiment, the plane is in 10° retroversion relative to a frontal and vertical plane. Referring to FIG. 33, the post holes 2036 define a locking structure 2038, discussed in more detail below. In addition, tangential to each post holes 2036 on diametrically opposite sides thereof are slots 2040 for receiving an alignment jig (not shown) to aid in drilling respective holes for cross pegs 2016.

Figure 35:
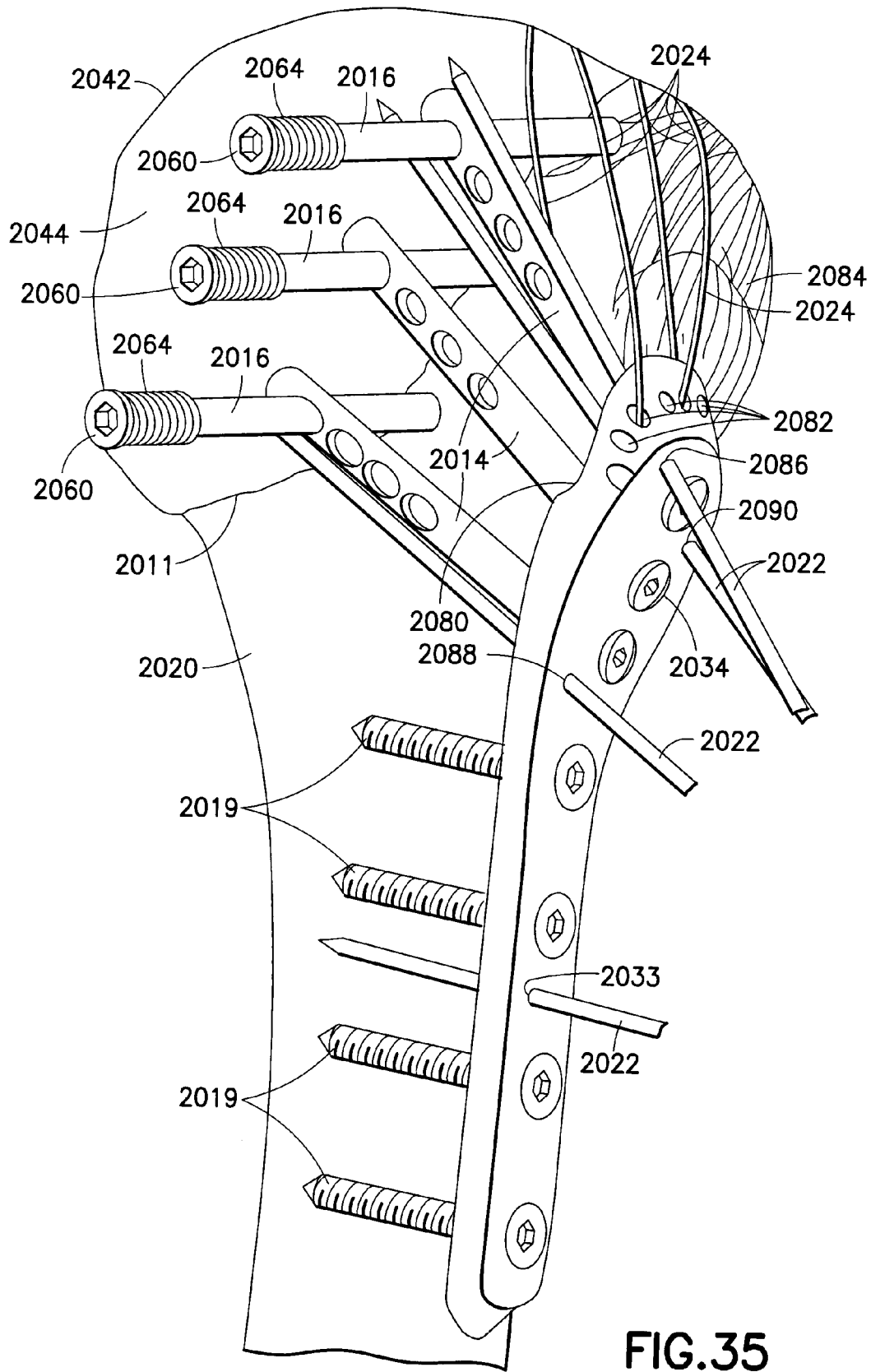
FIG. 35 illustrates the proximal humeral fracture fixation system of FIG. 32 implanted on the humerus to stabilize a fracture.

Referring to FIGS. 32 through 35, a tubular post 2014 is provided for each post hole 2036, and extends through the head portion 2034 of the plate 2012 generally perpendicular to the articular surface 2042 of the humeral head 2044 (FIG. 35). According to a preferred aspect of the invention, each post 2014 includes a head portion 2046 with slots 2048 which lock in a particular rotational orientation relative to the locking structure 2038 of the post hole 2036, similar to a bayonet lock. The post 2014 also includes a plurality of transverse, preferably parallel holes 2050 longitudinally displaced along the shaft 2052 of the post 2014. The post 2014 further includes an axial bore 2054 which extends from the head portion 2046 at least to the furthest transverse hole 2050, and an internal thread (not shown) below a driver recess 2056 and preferably below the slots 2048.

The cross pegs 2016 each include a head 2060 for receiving a driver, and a shaft portion 2062. The shaft portion 2062 is optionally threaded at 2064 adjacent the head 2060 for engagement with cancellous bone, but such is not required.

The cross pegs 2016 can be extended through a transverse hole 2050 in a post 2014 in the anterior-posterior plane and locked in place with a set screw 2018.

Referring to FIG. 34, the set screw 2018 includes a head 2066 with a driver recess 2068 and external threads 2070, and a shaft 2072. A set screw 2018 of appropriate length is inserted through the axial bore 2054 of the post 2014 until the end 2076 of the set screw 2018 contacts the portion of the shaft 2062 of the cross peg 2016 extending through a transverse hole 2050 of the post 2014. The set screw 2018 is threadably locked relative to the post 2014 to exert pressure on the cross peg 2016 and thereby retain the cross peg 2016. Set screws 2018 of various lengths may be provided for locking cross pegs in any of the longitudinally displaced transverse holes. Alternatively common length set screws may be cut down in size, if necessary, to the appropriate length prior to insertion through the bore 2054 of a post 2014. Where common length set screws 2018 are provided, the set screws 2018 may be scored along the shaft 2072 to facilitate breaking or cutting the set screws to appropriate length. In yet another alternative, the cross pegs may include transverse holes through which the set screws can be passed. In that manner common length set screws can be used, provided the cross pegs are rotationally aligned to receive the set screws through the transverse holes.

Referring to FIGS. 33 and 35, according to another preferred aspect of the invention, the head portion 2034 of the plate 2012 includes a lower proximal recess 2080 and a plurality of suture holes 2082 thereabout. The recess 2080 raises the proximal portion of the head portion 2034 of the plate 2012 off the surface of the bone (as shown in FIG. 35) to allow the surgeon to pass a needle (not shown) with suture material 2024 through the suture holes 2082 and between the plate 2012 and the bone 2020. In this manner, suture material 2024 can be used to secure tendons 2084 of the rotator cuff to the plate 2012 to place retaining force on smaller fragments of the fracture. The suture material 2024 is preferably metal braid or cable.

According to yet another aspect of the invention, the head portion 2034 includes a plurality of alignment holes 2086, 2088, and 2090 which are sized to closely receive individual K-wires in a particular orientation. The orientation of axes through the alignment holes 2086, 2088 and 2090, and consequently K-wires 2022 inserted therethrough, closely conforms to the space defined by the posts 2014 when coupled to the head portion 2034 of the plate 2012. More particularly, proximal alignment hole 2086 is located to define an axis which corresponds to the anterior-superior boundary of the posts 2014, distal alignment hole 2088 is located to define an axis which corresponds to the anterior-inferior boundary of the posts 2014, and relatively central alignment hole 2090 is located to define an axis which corresponds to the posterior boundary of the posts 2014.

In view of the above, according to another preferred method of stabilizing a fracture according to the invention, the fracture is reduced and the humeral plate 2012 is placed on the proximal humerus in an appropriate location (as discussed above), with the head portion 34 generally opposite the articular surface 2042. The head portion 2034 is then tacked onto the humeral head 2044 with K-wires 2022 drilled through the alignment holes 2086, 2088, 2090, and the shaft portion 2030 is preferably tacked to the distal fragment with one or more K-wires 2022, through K-wires holes 2033 in the shaft portion, or with one or more screws 2019 in the screw holes 2032. The fracture and location of the K-wires 2022 is examined, e.g., under fluoroscopy, to determine whether the fracture is reduced in an anatomically correct manner and if the K-wires 2022 are properly aligned relative to the anatomy. As indicated above, the fluoroscopically viewed K-wires 2022 provide an indication as to whether the posts 2014 will be properly oriented in relation to the fracture and the articular surface of the subchondral bone. If placement is not optimal, the K-wires 2022 can be removed and the surgeon has an opportunity to relocate and/or reorient the K-wires 2022 and drill again. Since each K-wire 2022 is of relatively small diameter relative to the posts 2014, the bone is not significantly damaged by the drilling process and the surgeon is not committed to the initial drill location and/or orientation.

Alternatively, shaft portion 2030 fixation may be delayed until after placement of the head portion 2034 of the plate 2012 is determined to be desirable (via visualization of the K-wires), and then preferably at least one cortical screw 2019 is inserted through a screw hole 2032 to stabilize the shaft portion 2030 to the humerus 2020.

Holes are then drilled through the post holes 2036 of the head portion 34 of the plate 2012 for the posts 2014. The holes are drilled across fracture 2011. The drill bit for drilling holes through the posts 2014 corresponds in diameter to the post holes 2036 such that no alignment jig is necessarily required, although one may be used is desired. The holes are drilled through the relatively soft spongy bone of the humeral head 2044 until the surgeon can 'feel' the harder cortex of the subchondral bone of the articular surface 2042. All posts holes may be drilled before proceeding. Alternatively, one post hole may be drilled, and for that post hole, a post can be inserted therein and coupled to the plate, an associated cross peg hole can be drilled, and a cross peg can be coupled to the post, as described in more detail below, prior to proceeding to drill the other post holes.

Assuming all post holes have been drilled, the posts 2014 are then inserted through the post holes 2036, and rotated to lock the heads 2046 of the posts 2014 relative to the locking structure 2038 of the head portion 2034 of the plate 2012. In contrast to a conventional threaded coupling, the locking coupling of 2046 and 2038 constrains the transverse holes 2050 to be in a predetermined rotational orientation relative to the plate 2012. A jig (not shown) is then coupled to the internal threads of a post 2014 and rotationally aligned relative to the tangential slots 2040 of the post hole 2036 to align a guide for drilling a hole in alignment with one of the transverse holes 2050 of that post 2014. Alternatively, the jig may be coupled directly the plate 2012. Once the hole is drilled into the bone, the jig is removed. A cross peg 2016 is then inserted through the drilled hole and extended through the transverse hole 2050 of that post 2014 such that the cross peg 2016 extends parallel to the articular surface 2042 of the humeral head 2044 on the opposite side of the fracture 2011 from the plate 2012.

The particular transverse hole 2050 in which a particular cross peg 2016 is inserted can be determined by the surgeon based upon the size of the humeral head 2044 and the location of the fracture. More particularly, it is desirable for each cross peg 2016 to extend just below the articular surface 2042. If the cross peg 2016 is within the articular surface 2042 it will cause interference with the joint. If the cross peg 2016 is too far away from the articular surface 2042, there will be too much spongy bone between the hard articular surface 2042 and the cross peg 2016 which could cause the fractured humeral head 2044 to collapse. During insertion of the cross pegs 2016, the cross pegs 2016 are subject to little resistance through the drilled holes and the surgeon has tactile sensation as to when the cross pegs 2016 have been extended through the appropriate transverse holes 2050 and when the ends of the cross pegs 2016 have reached hard cortical bone. It is undesirable to force the cross pegs through the cortical bone such that the ends of the cross pegs 2016 are exposed.

Once the cross peg 2016 is properly positioned, it is desirable to lock it in position. The set screw 2018 is inserted through the axial bore 2054 of the post 2014 and threadably coupled to the post 2014 such that the end of the set screw 2018 seats against the cross peg 2016 locking the cross peg in place. The process is repeated for the other posts 2014 and cross pegs 2016.

The K-wires 2022 are removed. The sutures 2024 are added, and the remaining cortical screws 2019, if not already inserted, are inserted to further stabilize the fracture.

With the fixation system implanted, the posts 2014 are oriented perpendicular to the articular surface 2042 but do not extend far enough to break through the articular surface. The plate 2012 and cross pegs 2016 sandwich the fracture 2011 to provide a stabilizing framework. The cross pegs 2016 extending through the transverse holes 2050 in the posts 2014 are oriented parallel to the articular surface 2042 and provide a structure which locks the plate relative to the bone. Furthermore, such placement and orientation of the cross pegs 2016 will not result in any damage to, irritation to, or interference with the articular surface of the shoulder joint.

Figure 36:
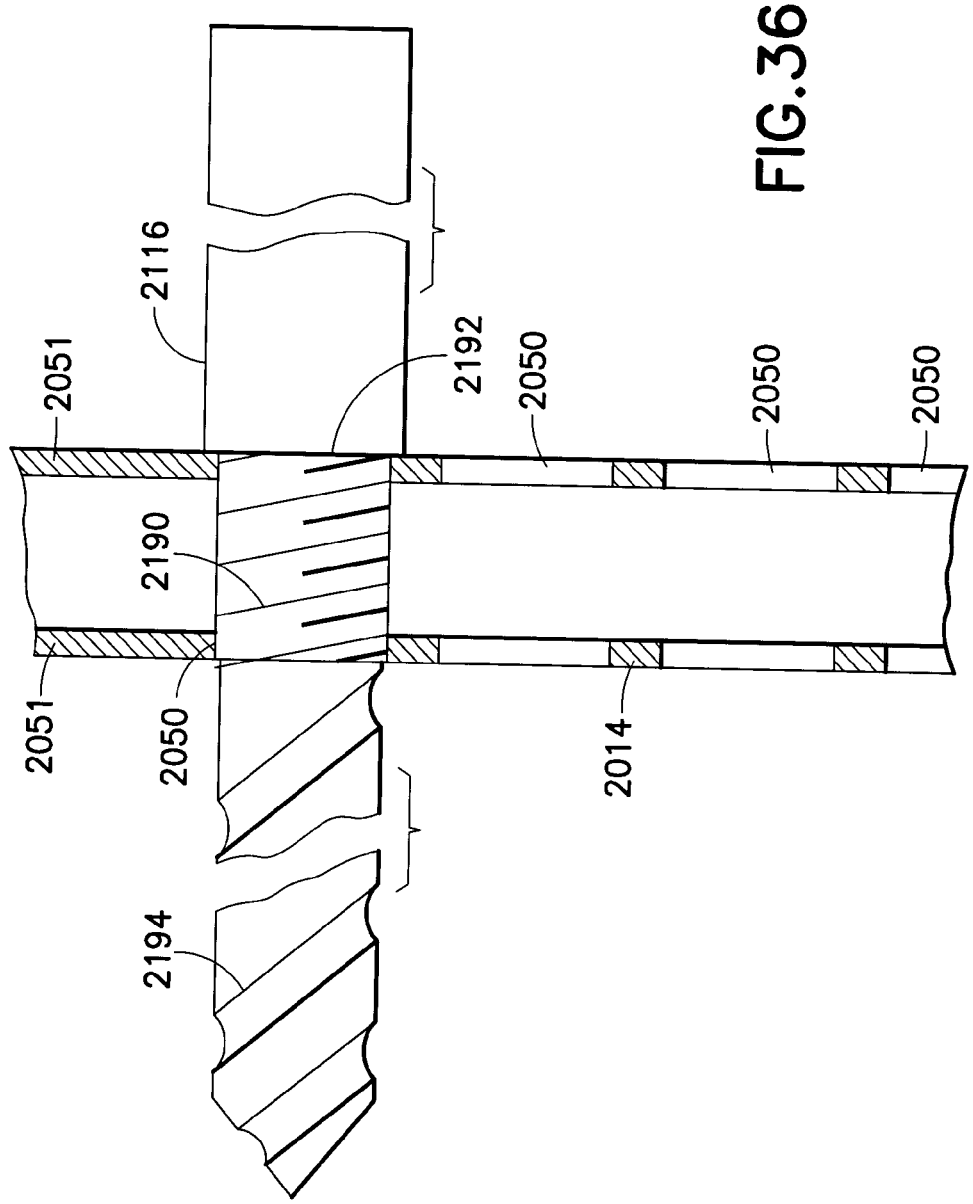
FIG. 36 is a schematic view of an alternate embodiment of a cross peg for use in a fixation system according to the invention.

Referring now to FIG. 36, an alternative embodiment of a cross peg 2116 for the fracture fixation system is shown. In the alternative embodiment, no set screw is required to secure the cross peg within the post. The cross peg 2116 includes threads 2190 along a central portion of its shaft which are preferably self-tapping and spaced appropriately to engage the wall 2051 surrounding the holes 2050 of the post 2014. However, this threaded engagement may limit the surgeon's tactile sensation of when the far cortex is reached by the cross peg. In view thereof, the cross peg 2116 may be provided with a shoulder 2192 that limits its introduction, i.e. such that the shoulder 2192 can not extend through the transverse hole 2050. In addition, the cross peg 2116 may include cutting flutes 2194 which permit drill-less introduction.

As yet another alternative, the transverse holes may be provide with machine threads, and the cross pegs may be likewise threaded with machine threads such that the cross peg and post can threadably engage together without the cross peg tapping into the post.

Furthermore, any of the above described cross pegs may be headless. In such a configuration, the cross peg is adapted to be seated beneath the surface of the bone. Thus, such a cross is suited to extend through the articular surface without interference with the shoulder joint if extension of a cross peg through the articular surface is necessary or desirable for stabilization of a particular fracture with the system of the invention.

Figure 37:
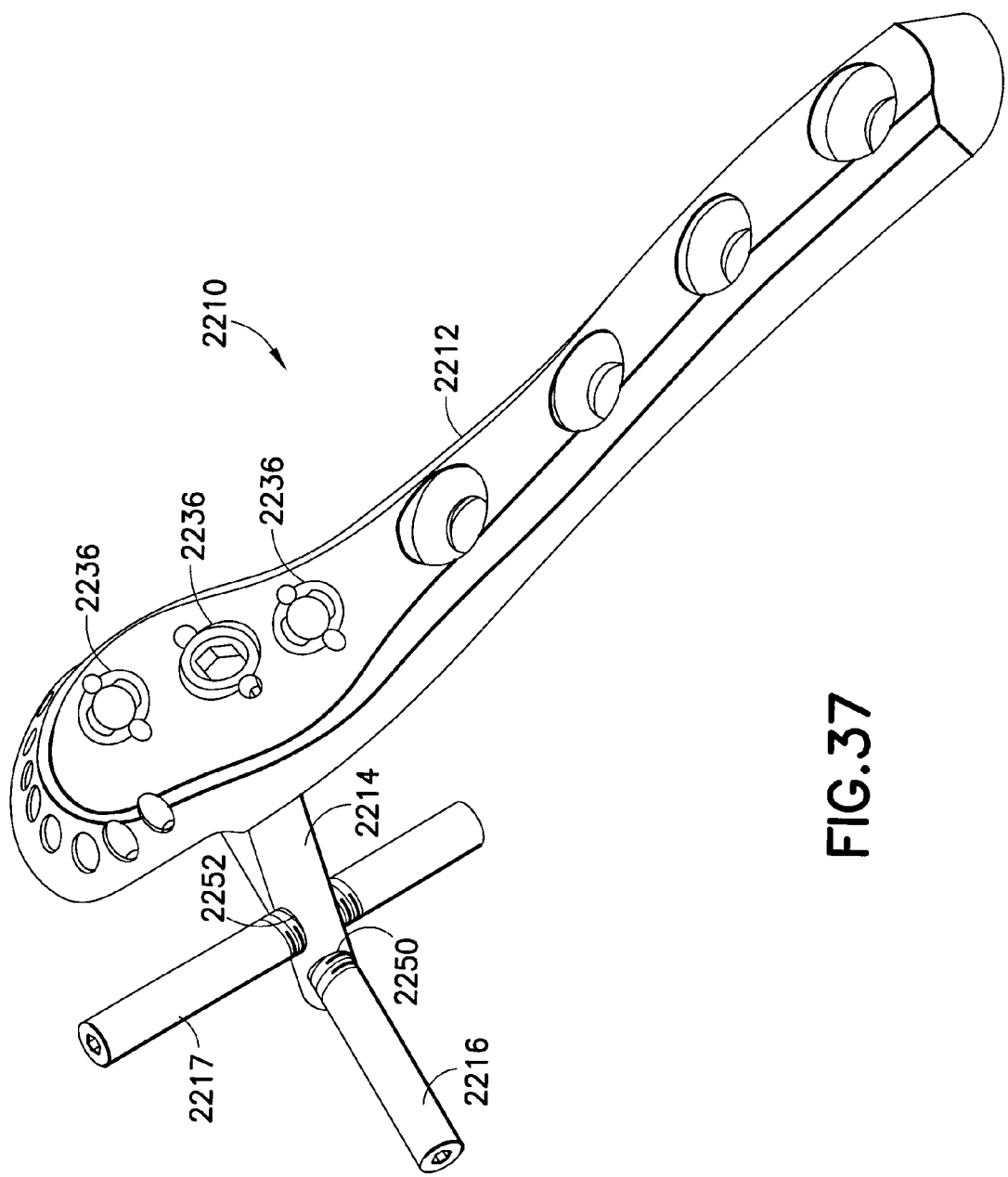
FIG. 37 is a perspective view of another embodiment of a proximal humeral fixation system according to the invention.

Turning now to FIG. 37, another embodiment of a humeral fracture fixation system 2210 according to the invention is shown. In system 2210, a single post 2214 may be inserted through any of the post holes 2236 in plate 2212, although only a single post hole is required in this embodiment. The post 2214 includes holes 2250, 2252 which are oriented transverse to each other, preferably at 90°, and preferably perpendicular to the longitudinal axis of the post 2214. Cross pegs 2216, 2217 are then inserted through holes 2250, 2252 and preferably locked relative to the post. Cross peg 2216 extends parallel to the anterior-posterior plane of the articular surface, and cross peg 2217 extends parallel to the relatively transverse plane. In this embodiment, it is not practical to lock the distal cross peg 2216 with a set screw. Thus, it may be desirable for one or both of the cross pegs to thread into or relative to the post 2214. Cross pegs 2216, 2217 are also shown in a headless design, described above, which can be seated beneath the surface of the bone and provide no interference with the articular surface.

Figure 38:
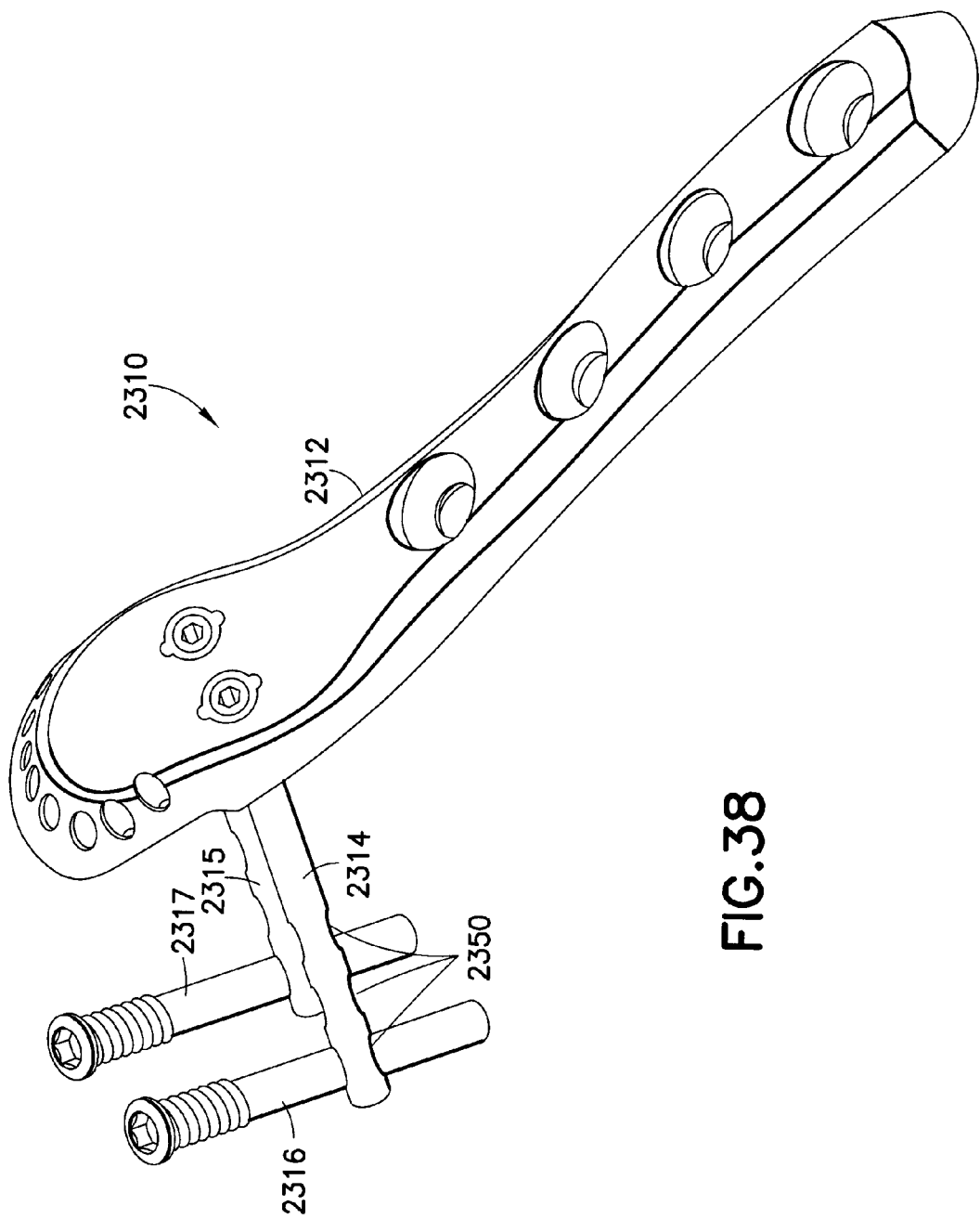
FIG. 38 is a perspective view of another embodiment of a proximal humeral fixation system according to the invention.

Referring now to FIG. 38, another embodiment of humeral fracture fixation system 2310 according to the invention is shown. In system 2310, two laterally offset posts 2314, 2315 are displaced in an anterior-posterior plane. The posts are preferably angled relative to each other in the same plane by, e.g., 20° to 90°. Alternatively, the posts 2314, 2315 may be vertically offset in the proximal-distal plane. Each of the posts 2314, 2315 has at least one transverse hole 2350, with an axis therethrough preferably oriented substantially transverse to the anterior-posterior plane when the system 2310, with plate 2312, is implanted at the shoulder, and may have a plurality of such holes 2350 longitudinally displaced along the post. A cross peg 2316, 2317 is inserted through a selected one of the holes 2350 in each post 2314, 2315.

Figure 39:
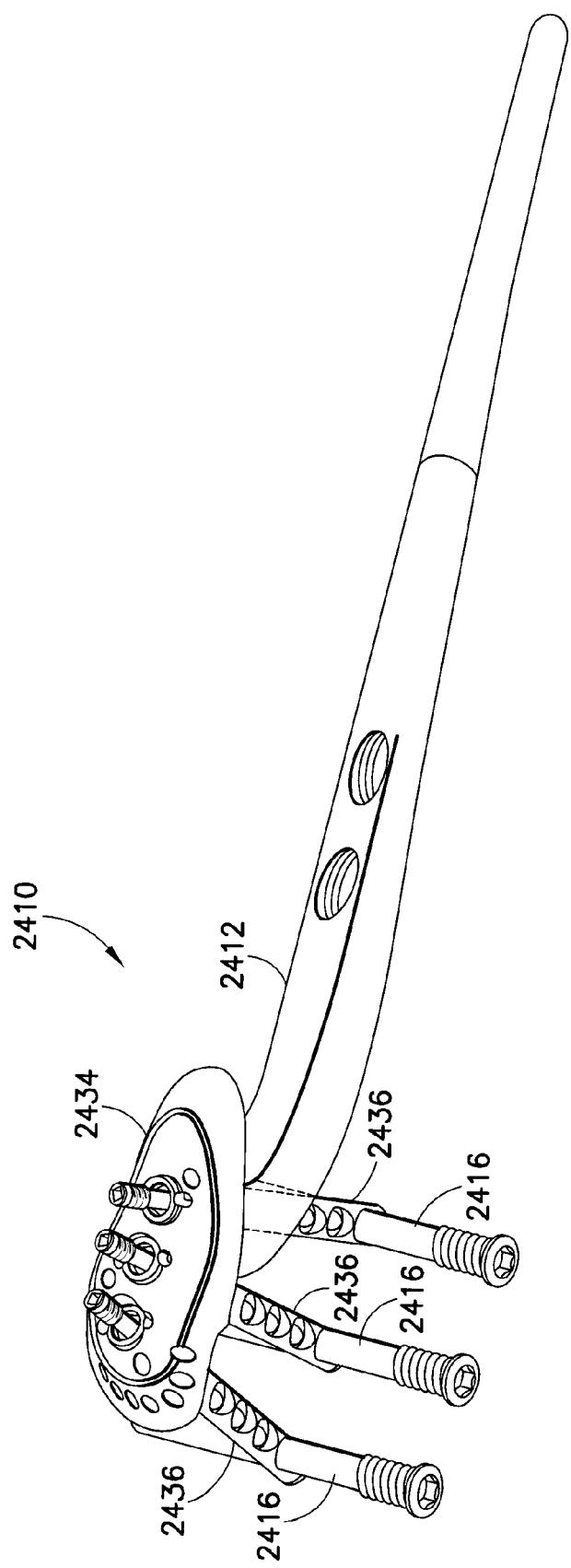
FIG. 39 is a perspective view of another nail-plate embodiment of a proximal humeral fixation system according to the invention.

Turning now to FIG. 39, another nail-plate embodiment of humeral fracture fixation system 2410 is shown. System 2410 may include any of the post and cross peg configurations discussed above (e.g., posts 2436 and pegs 2416), any other transverse scaffold construction that captures the fracture between the plate-like head portion 2434 of the device 2412 and one or more cross pegs, or any post with a deployable supports/anchors.

There have been described and illustrated herein embodiments of fracture fixation systems and methods of stabilizing a fracture, particularly of the humerus. While particular embodiments of the invention have been described, it is not intended that the invention be limited thereto, as it is intended that the invention be as broad in scope as the art will allow and that the specification be read likewise. Thus, while the preferred embodiments are for humeral fracture fixation systems, it is appreciated that the system is well adapted to bone fractures of any articular surface having a convex shape. Thus, the system of the invention could similarly be used to treat a fracture of the femoral head. In such variation, the angle between the head and shaft portions may be different so that the head portion properly seats on the anatomy. In addition, while a particular number of posts and cortical screws have been disclosed in relation to particular embodiments, it will be understood that only one post is required, and fewer or more cortical screw holes can be provided and/or screws can be used. Furthermore, while cortical screws are disclosed for coupling the shaft portion to the bone, other fasteners can likewise be used. Moreover, while the terms 'posts' and 'pegs' have been used to described particular elements of the invention, it is understood that such terms are used as a matter of convenience, and are not intended to confer particular structure when used in the claims. Thus, what is referred to as a 'post' is intended to broadly read on any rigid shaft-like fastener coupled to the plate. Also, what is referred to as a 'peg' is intended to broadly read on any shaft-like element which extends in transverse relation one of the posts and is (i) coupled to such post and/or (ii) extends through a transverse hole formed within the post. Thus, the peg may be a screw, a non-threaded rod, a K-wire, etc.

Furthermore, while left-hand humeral plates are shown, it is recognized that right-hand humeral plates are generally mirror-images of the illustrated left-hand plates. Moreover, while the system has been described for use with respect to fractures, it is appreciated that it may also be used in the treatment of osteotomies and non-unions of the proximal humerus and other bones having an articular surface with a convex shape. It will therefore be appreciated by those skilled in the art that yet other modifications could be made to the provided invention without deviating from its scope as claimed.

What is claimed is:

1. A fracture fixation system for use in stabilizing a fracture at the metaphysis of a bone, the metaphysis having subchondral bone defining a convex articular surface, comprising:
   a) a rigid plate including a head portion with a post hole, and a shaft portion with at least one bone screw hole;
   b) a post insertable into said post hole extendable toward the articular surface of the bone; and
   c) rigid supports deployable and extendable from said post for supporting the subchondral bone, said supports each have a bone piercing end, an opposite back end, a non-deployed position, and a deployed position with said supports extending from said post, and when said supports are advanced from said non-deployed position to said deployed position, said back end is advanced distally relative to said post.

2. A fracture fixation system according to claim 1, wherein:
   said supports are fixed in a curved configuration.

3. A fracture fixation system according to claim 1, wherein:
   said supports include at most two supports.

4. A fracture fixation system according to claim 1, wherein:
   said supports are substantially contained within said post prior to deployment.

5. A fracture fixation system according to claim 1, wherein:
   said supports are at least partially within said post prior to deployment.

6. A fracture fixation system according to claim 1, further comprising:
   means couplable to said post for deploying said supports.

7. A fracture fixation system according to claim 1, further comprising:
   a set screw, wherein said post includes a longitudinal bore and said set screw is insertable into said longitudinal bore in said post to deploy said supports.

8. A fracture fixation system according to claim 1, wherein:
   said plate is sized for placement on the proximal humerus.

9. A fracture fixation system according to claim 1, wherein:
   said post is a tubular construct including proximal and distal ends, a plurality of peripheral windows, and a longitudinal bore, and
   said supports are pivotally coupled relative to said post and laterally extendable at said windows.

10. A fracture fixation system according to claim 1, wherein:
    said post has an outer surface with a diameter, and
    said supports in said deployed position extend from said outer surface of said post in diametrically opposite directions, each support extending by a radial distance at least as large as said diameter.

11. A fracture fixation system according to claim 1, wherein:
    said supports are curved and have a concave side and a convex side, said convex and concave sides extending between said bone piercing end and said back end,
    wherein when said supports are in said deployed position, said concave side is directed toward said plate and said convex side is directed away from said plate.

12. A fracture fixation system according to claim 1, wherein:
    said supports consist of two supports deployable and extendable from said post.

13. A fracture fixation system for use in stabilizing the metaphysis of a bone, the metaphysis having subchondral bone defining a convex articular surface, comprising:
    a) an orthopedic implant including a head portion with a post hole, and a shaft portion with at least one bone screw hole;
    b) a post insertable into said post hole and extendable toward the articular surface of the bone; and
    c) rigid supports deployable and extendable from said post for supporting the subchondral bone, said supports each have a bone piercing end, an opposite back end, a non-deployed position, and a deployed position with said supports extending from said post, and when said supports are advanced from said non-deployed position to said deployed position, said back end is advanced distally relative to said post.

14. A fracture fixation system according to claim 13, wherein:
    said post has an outer surface with a diameter, and
    said supports in said deployed position extend from said outer surface of said post in diametrically opposite directions, each support extending by a radial distance at least as large as said diameter.

15. A fracture fixation system according to claim 13, wherein:
    said supports are curved and have a concave side and a convex side, said convex and concave sides extending between said bone piercing end and said back end,
    wherein when said supports are in said deployed position, said concave side is directed toward said implant and said convex side is directed away from said implant.

16. A fracture fixation system according to claim 13, wherein:
    said supports consist of two supports deployable and extendable from said post.

* * * * *